US008722870B2

(12) United States Patent
Witte et al.

(10) Patent No.: US 8,722,870 B2
(45) Date of Patent: May 13, 2014

(54) NUCLEIC ACIDS ENCODING INTERFERON ALPHA ANTIBODIES

(71) Applicant: Medarex, Inc, Princeton, NJ (US)

(72) Inventors: Alison J. Witte, Scotts Valley, CA (US); Denise Williams, San Jose, CA (US); Josephine M. Cardarelli, San Carlos, CA (US); David King, Belmont, CA (US); David B. Passmore, San Carlos, CA (US)

(73) Assignee: Medarex, L.L.C., Princeton, NJ (US)

( * ) Notice: Subject to any disclaimer, the term of this patent is extended or adjusted under 35 U.S.C. 154(b) by 0 days.

(21) Appl. No.: 13/909,608

(22) Filed: Jun. 4, 2013

(65) Prior Publication Data

US 2013/0254912 A1 Sep. 26, 2013

Related U.S. Application Data

(60) Continuation of application No. 13/211,092, filed on Aug. 16, 2011, now Pat. No. 8,475,797, which is a continuation of application No. 12/551,250, filed on Aug. 31, 2009, now Pat. No. 8,025,882, which is a division of application No. 11/009,410, filed on Dec. 10, 2004, now Pat. No. 7,741,449.

(60) Provisional application No. 60/528,757, filed on Dec. 10, 2003.

(51) Int. Cl.
*C07H 21/04* (2006.01)
*C12N 15/63* (2006.01)
*C12N 1/20* (2006.01)

(52) U.S. Cl.
USPC .................. 536/23.53; 435/320.1; 435/252.1

(58) Field of Classification Search
None
See application file for complete search history.

(56) References Cited

U.S. PATENT DOCUMENTS

| | | | |
|---|---|---|---|
| 4,423,147 A | 12/1983 | Secher et al. | |
| 4,902,618 A | 2/1990 | Berg | |
| 4,973,556 A | 11/1990 | Bove et al. | |
| 6,007,805 A | 12/1999 | Foster et al. | |
| 6,458,932 B1 | 10/2002 | Novick et al. | |
| 6,475,983 B1 | 11/2002 | Eid et al. | |
| 7,087,726 B2 | 8/2006 | Chuntharapai et al. | |
| 7,741,449 B2 | 6/2010 | Witte et al. | |
| 8,025,882 B2 | 9/2011 | Witte et al. | |
| 8,475,797 B2 | 7/2013 | Witte et al. | |
| 2003/0166228 A1 | 9/2003 | Chuntharapai et al. | |

FOREIGN PATENT DOCUMENTS

| | | |
|---|---|---|
| CN | 1324838 | 12/2001 |
| CN | 1416894 | 5/2003 |
| EP | 0 633 931 | 5/2003 |
| JP | 5047626 | 10/2012 |
| WO | WO 92/18626 | 10/1992 |
| WO | WO 93/04699 | 3/1993 |
| WO | WO 93/20187 | 10/1993 |
| WO | WO 95/07716 | 3/1995 |
| WO | WO 95/24212 | 9/1995 |
| WO | WO 97/41229 | 11/1997 |
| WO | WO 98/24884 | 6/1998 |
| WO | WO 01/09187 | 2/2001 |
| WO | WO 02/043478 | 6/2002 |
| WO | WO 02/066649 | 8/2002 |

OTHER PUBLICATIONS

U.S. Appl. No. 11/009410 (US 7,741,449), filed Dec. 10, 2004, (Jun. 22, 2010).
U.S. Appl. No. 12/551250 (US 8,025,882), filed Aug. 31, 2009 (Sep. 27, 2011).
U.S. Appl. No. 13/211092 (US 8,475,797), filed Aug. 16, 2011 (Jul. 2, 2013).
U.S. Appl. No. 11/009410, Aug. 18, 2009, Issue Fee payment.
U.S. Appl. No. 11/009410, May 18, 2009, Notice of Allowance.
U.S. Appl. No. 11/009410, Feb. 19, 2009, Response to Non-Final Office Action.
U.S. Appl. No. 11/009410, Sep. 29, 2008, Non-Final Office Action.
U.S. Appl. No. 11/009410, Jun. 25, 2008, Amendment and Request for Continued Examination (RCE).
U.S. Appl. No. 11/009410, Jan. 25, 2008, Final Office Action.
U.S. Appl. No. 11/009410, Nov. 12, 2007, Response to Non-Final Office Action.
U.S. Appl. No. 11/009410, Jul. 10, 2007, Non-Final Office Action.
U.S. Appl. No. 12/551250, Aug. 16, 2011, Issue Fee payment.
U.S. Appl. No. 12/551250, Jun. 9, 2011, Response to Amendment under Rule 312.
U.S. Appl. No. 12/551250, Jun. 2, 2011, Amendment after Notice of Allowance.
U.S. Appl. No. 12/551250, May 18, 2011, Notice of Allowance.
U.S. Appl. No. 12/551250, Mar. 3, 2011, Response to Non-Final Office Action.
U.S. Appl. No. 12/551250, Nov. 12, 2010, Non-Final Office Action.
U.S. Appl. No. 12/551250, Aug. 23, 2010, Response to Restriction Requirement.
U.S. Appl. No. 12/551250, Jun. 25, 2010, Restriction Requirement.
U.S. Appl. No. 13/211092, Jun. 3 2013, Issue Fee payment.

(Continued)

*Primary Examiner* — Sharon Wen
(74) *Attorney, Agent, or Firm* — Baker Botts L.L.C.

(57) ABSTRACT

The present invention provides isolated anti-interferon alpha monoclonal antibodies, particularly human monoclonal antibodies, that inhibit the biological activity of multiple interferon (IFN) alpha subtypes but do not substantially inhibit the biological activity of IFN alpha 21 or the biological activity of either IFN beta or IFN omega. Immunoconjugates, bispecific molecules and pharmaceutical compositions comprising the antibodies of the invention are also provided. The invention also provides methods for inhibiting the biological activity of IFN alpha using the antibodies of the invention, as well as methods of treating disease or disorders mediated by IFN alpha, such as autoimmune diseases, transplant rejection and graft versus host disease, by administering the antibodies of the invention.

20 Claims, 12 Drawing Sheets

(56) References Cited

OTHER PUBLICATIONS

U.S. Appl. No. 13/211092, Mar. 4, 2013, Notice of Allowance.
U.S. Appl. No. 13/211092, Feb. 22, 2013, Terminal Disclamer Review Decision.
U.S. Appl. No. 13/211092, Feb. 20, 2013, Amendment and Terminal Disclaimer filed.
The Merck Manuals Online Medical Library, [online]. Whitehouse Station, NJ: Merck Research Laboratories, 2006-2007. [retrieved on 202/Apr. 2008]. Retrieved from the Internet: <URL: http://www.merck.com/mmpe/print/sec04/ch032g.html>. Systemic Lupus Erythematosus (SLE), see pp. 1-6.
Adolf et al., 1982, "Production of Monoclonal Antibodies to Human IFN-α and Their use for Analysis of the Antigenic Composition of Various Natural Interferons," *Journal of Cellular Physiology Supplement*, vol. 2: p61-68.
Allen et al., 1982, "Analysis and Purification of Human Lymphoblastoid (Namalwa) Interferon Using a Monoclonal Antibody," *J gen. Virol.*, vol. 63: p207-212.
Allen et al., 1982, "Structure and properties of human interferon-α from Namalwa lymphoblastoid cells," *Biochem.J.*, vol. 207: p397-408.
Amici et al., 2000, "Human erythrocyte pyrimidine 5'-nucleotidase, PN-1, is identical to p36, a protein associated to lupus inclusion formation in response to α-interferon," *Blood*, vol. 96, No. 4: p1596-1598.
Andzhaparidze et al., 1988, "Preparation of Hybridomas producing monoclonal antibodies against human interferon," *Acta Virol*, vol. 32, No. 6: p481-6.
Barasoain et al., 1989, "Antibodies Against a Peptide Representative of a Conserved Region of Human IFN-α," *The Journal of Immunology*, vol. 143, No. 2: p507-512.
Barbas et al. PNAS 1995, 92:2529-2533.
Batteux et al., 1999, "FCgammaR11 (CD32)-dependent induction of interferon-alpha by serum from patients with lupus erythematosus," *European Cytokine Network*, vol. 10, No. 4: p509-514.
Bave et al., 2000, "The Combination of Apoptotic U937 Cells and Lupus IgG Is a Potent IFN-α Inducer, *The Journal of Immunology*," vol. 165: p3519-3526.
Beiboer et al. J. Mol. Biol. 2000, 296:833-849.
Belardelli et al., 1987, "Studies on the Expression of Spontaneous and Induced Interferons in Mouse Peritoneal Macrophages by Means of Monoclonal Antibodies to Mouse Interferons," *J gen. Viral*, vol. 68: p2203-2212.
Bennett; J. Exp Med 2003;197(6);771-723.
Berthold et al., 1985, "Immunoassay for the Quantitation of Human Leukocyte Interferon," *Arzneim-Forsch./Drug Res.*, vol. 35: p364-369.
Bigazzi, 2005, "Murine lupus induced by tetramethylpentadecane: an animal model of systemic human autoimmunity," *Clinical Immunology*, vol. 114: p97-99.
Blanco et al., Science 2001;294:1540-1543.
Blank et al., 1999, "Identification of a linear epitope of interferon-α2b recognized by neutralizing monoclonal antibodies," *Eur. I Biochem*, vol. 265: p11-19.
Boyman et al., 2004, "Spontaneous Development of Psoriasis in a New Animal Model Shows an Essential Role for Resident T Cells and Tumor Necrosis Factor-α," *J. Exp. Med.*, vol. 199, No. 5; p731-736.
Brunner et al., 1999, "Sensitivity of the Systemic Lupus Erythematosus Disease Activity Index, British Isles Lupus Assessment Group Index, and Systemic Lupus Activity Measure in the Evaluation of Clinical Change in Childhood-Onset Systemic Lupus Erythematosus," *Arthritis & Rheumatism*, vol. 42, No. 7: p1354-1360.
Chen et al., 2000, "The relationship between Th1/Th2-type cells and disease activity in patients with systemic lupus erythematosus," *Chinese Medical Journal*, vol. 113, No. 10: p877-880.
Chen et al., EMBO J. 1993; 821-830.

Chuntharapai et al., 2001, "Characterization and Humanization of a Monoclonal Antibody That Neutralizes Human Leukocyte Interferon: A Candidate Therapeutic for IDDM and SLE," CYTOKINE, vol. 15, No. 5: p250-260.
Cook et al., J Biol Chem. 1996; 271:13448.
International Search Report for PCT/US04/41777, dated Oct. 31, 2005.
Corzillius et al., 1999, "Responsiveness and sensitivity to change of SLE disease activity measures," *Lupus*, vol. 8: p655-659.
Crow, 2003, "Interferon-α: A New Target for Therapy in Systemic Lupus Erythematosus?," *Arthritis & Rheumatism*, vol. 48, No. 9: p2396-2401.
Csabayováet al., 1995, "Relativity of an Antigenic Homology Between Human Interferon-α1 and Interferon-α2c," *Immunological Investigations*, vol. 24, No. 5: p787-793.
Cutrone and Langer, J Biol Chem. 2001; 276:17140.
Dean et al., 2000, "Cytokines and systemic lupus erythematosus," *Ann Rheum Dis.*, vol. 59: p243-251.
Exley et al., 1984, "A Comparison of the Neutralizing Properties of Monoclonal and Polyclonal Antibodies to Human Interferon Alpha," *J. gen. Viral.*, vol. 65: p2277-2280.
Fishwild et al., Nature Biotechnology. 1996; 14:845-851.
Foulis et al., Lancet. 1987; 2: 1423.
Furukawa et al., 2005, "Animal models of spontaneous and drug-induced cutaneous lupus erythematosus," *Autoimmunity Reviews*, vol. 4: p345-350.
Greensberg et al., 2005, "Interferon-α/β-Mediated Innate Immune Mechanisms in Dermatomyositis," *Ann Neural*, vol. 57: p664-678.
Gren et al., 1984, "Novel Human Leukocyte Interferon Subtype and Structural Comparison of Alpha Interferon Genes," *Journal of Intereron Research*, vol. 4: p609-617.
Griffiths et al., 2005, "Assessment of patients with systemic lupus erythematosus and the use of lupus disease activity indices," vol. 19, No. 5: p685-708.
Grossberg et al., 2001, "The Neutralization of Interferons by Antibody. I. Quantitative and Theoretical Analyses of the Neutralization Reaction in Different Bioassay Systems," *Journal of Interferon and Cytokine Research*, vol. 21: p729-742.
Grossberg et al., 2001, "The Neutralization of Interferons by Antibody. II. Neutralizing Antibody Unitage and Its Relationship to Bioassay Sensitivity: The Tenfold Reduction Unit," *Journal of Interferon and Cytokine Research*, vol. 21: p743-755.
Hooks et al., Arthritis Rheum. 1982;25:396.
Hron et al., 2004, "Type I IFN Protects Against Murine Lupus," *The Journal of Immunology*, vol. 173: p2134-2142.
Huang et al., 1995, "Interferon Expression in the Pancreases of Patients With Type I Diabetes," vol. 44: p658-664.
Huang et al., 1994, "Islet Expression of Interferon-α-Precedes Diabetes in Both the BB Rat and Streptozotocin-Treated Mice," *Immunity*, vol. 1: p469-478.
Hueber et al., 2004, "Interferon-α-Inducible Proteins Are Novel Autoantigens in Murine Lupus," vol. 50, No. 10: p3239-3249.
Isenberg et al., 2000, "From BILAG to BLIPS-disease activity assessment in lupus past, present and future," *Lupus*, vol. 9: p651-654.
Jahnsen et al., 2002, "Involvement of Plasmacytoid Dendritic Cells in Human Diseases," *Human Immunology*, vol. 63: p1201-1205.
Kandefer-Szerszen et al., 1992, "Three Seperate Epitopes on Human IFN—αVariants Defined by Monoclonal Antibodies and Their Role in the Binding to Receptors," *Archivum Immunologiae et Therapiae Experimentalis*, vol. 40: p241-246.
Kawade, 1980, "An Analysis of Neutralization Reaction of Interferon by Antibody: A Proposal on the Expression of Neutralization Titer," *Journal of Interferon Research*, vol. 1, No. 1: p61-70.
Kawade et al., 1980, "Antigenic Relationships Among Various Interferon Species," *Annals of the New York Academy of Sciences*, vol. 350, No. 1: p:422-427.
Kawade et al., 1981, "Antigenic Cross-Reaction Between the α Types of Human and Mouse Interferon," *Antiviral Research*, vol. 1: p167-178.
Kawade et al., 1984, "Neutralization of Interferon by Antibody: Appraisals of Methods of Determining and Expressing the Neutralization Titer," *Journal of Interferon Research*, vol. 4: p571-584.

(56) References Cited

OTHER PUBLICATIONS

Kawade, 1985, "Neutralization of activity of effector protein by monoclonal antibody: formulation of antibody dose-dependence of neutralization for an equilibrium system of antibody, effector, and its cellular receptor," *Immunology*, vol. 56: p497-504.

Kawade et al., 1985, "The nature of neutralization reactioin between effector protein and monoclonal antibody: a quantitative study of neutralization characteristics of anti-interferon antibodies," *Immunology*, vol. 56: p489-495.

Kirou et al., 2004, "Coordinate Overexpression of Interferon-a-Induced Genes in Systemic Lupus Erythematosus," *Arthritis & Rheumatism*, vol. 50, No. 12: p3958-3967.

Klimka et al., 2000, "Human anti-CD30 recombinant antibodies by guided phage antibody selection using cell panning," *British Journal of Cancer*, vol. 83, No. 2: p252-260.

Kontsek et al., 1989, "Monoclonal Antibodies Neutralizing Human Leukocyte Acid-and Thellnolabile Interferon Alpha," *Acta virol.*, vol. 33: p254-261.

Kontsek et al., 1991, "Enhancement of neutralizing efficacy by combining three monoclonal antibodies to human interferon-alpha," *Immunology*, vol. 73: p8-11.

Krueger et al., 2005, "Psoriasis pathophysiology: current concepts of pathogenesis," *Ann Rheum Dis*, vol. 64, Suppl. II: ii30-ii36.

Kwant et al., 2004, "Behavioral effects of infection with interferon-gamma adenovector," *Behavioural Brian Research*, vol. 151: p73-82.

Lamminmaki et al. JBC 2001,276:36687-36694.

Laurent et al., 1982, "Characterization of Monoclonal Antibody Specific for Human Alpha Interferon," *Hybridoma*, vol. 1, No. 3: p313-322.

Laurent et al., 1984, "Purification of the Major Species of Human Leucocyte Interferon With the Help of a Monoclonal Antibody," *Develop. biol. Standard*, vol. 57: p305-310.

Lazar et al., 2006, "Engineered antibody Fc variants with enhanced effector function," PNAS, vol. 103, No. 11: p4005-4010.

Lederman et al. Molecular Immunology 28: 1171-1181, 1991.

Lewerenz et al., J Mol Biol. 1998;282:585.

Li et al., 2004, "Induction of systemic lupus erythematosus syndrome in BALB/c mice by immunization with active chromatin," *Acta Pharmacol Sin*, vol. 25, No. 6: p807-811.

Li et al. PNAS 77: 3211-3214,1980.

Lonberg et al., Nature. 1994;368(6474):856-859.

Lu et al., 2000, "Regulation of the Promoter Activity of Interferon Regulatory Factor-7 Gene," vol. 275, No. 41: p31805-31812.

Lydon et al., 1985, "Immunochemical Mapping of α-2 Interferon," *Biochemistry*, vol. 24: p4131-4141.

MacCallum et al. J. Mol. Biol. 1996,262:732-745.

Männel et al., 1982, "A rat monoclonal antibody against mouse α and β interferon of all molecular weight species," *Nature*, vol. 296: p664-665.

Mathian et al., 2005, "IFN-α Induces Early Lethal Lupus in Preautoimmune (New Zealand Black×New Zealand White)F but Not in BALB/c Mice," *The Journal of Immunology*, vol. 174: p2499-2506.

McMullen et al., 1990, "Antipeptide Antibodies Against Conserved Regions of Human Interferons-α Evidence for Conformational Variations Between IFN-α Subtypes," *Biochemistry International*, vol. 21, No. 2: p261-269.

Meager et al., 1986, "Epitope Localization of a Monoclonal Antibody, LO-22, with Broad Specificty for Interferon-α Subtypes," *Journal of Interferon Research*, vol. 6: p729-736.

Mogensen et al., J Interferon Cytokine Res. 1999;19:1069.

Monteleone et al., 2001, "Interferon-α drives T cell-mediated immunopathology in the intestine," *Eur: J. Immunol.*, vol. 31: p2247-2255.

Morser et al., 1981, "Production and Screening of Cell Hybrids Producing a Monoclonal Antibody to Human Interferon-α," *J. gen. Virol.*, vol. 53: p257-265.

Nestle et al., 2005, "Plasmacytoid predendritic cells initiate psoriasis through interferon-α production," *JEM*, vol. 202, No. 1: p135-143.

Noll et al., 1989, "Production and characterization of four monoclonal antibodies specific for human interferon-alpha-1 and -alpha-2," *Biomed. Biochem. Acta*, vol. 48: p165-176.

Nolte et al., 1994, "Different Specificities of SLE-Derived and Therapy-Induced Interferon-α Antibodies," *Journal of Interferon Research*, vol. 14: p197-199.

Nosik et al., 1985, "Testing of monoclonal antibodies to human interferon," *Vopr Virusol*, vol. 30, No. 5: p600-2 [Abstract Only].

Notani et al., 1989, "Application of Namalva Interferon-α Monoclonal Antibodies for Purification and Enzyme Immnoassay of Interferon-α," *Journal of Immunoassay*, vol. 10, No. 2&3: p257-276.

Novék et al., 1986, "Preparation and Characterization of Hybridomas Producing Monoclonal Antibodies Against Human Alpha Interferon," *Acta virol.*, vol. 30: p228-233.

Novick et al., Cell. 1994; 77:391.

Novik et al., 1982, "Monoclonal Antibodies to Human α-Interferon and Their Use for Affinity Chromatography, " *The Journal of Immunolgy*, vol. 129, No. 5; p2244-2247.

Overall et al., 1992, "Functional Analysis of Interferon-α4a-Subtype Reactivity, Neutralisation of Biological Activities and Epitope Analysis," *Molecular Immunology*, vol. 23, No. 3: p391-399.

Padlan et al. PNAS 1989, 86:5938-5942.

Panem et al., 1983, "Renal Deposition of Alpha Interferon in Systemic Lupus Erythematosus," *Infection and Immunity*, vol. 42, No. 1: p368-373.

PBL, 1998 "Your Total Interferon Source: 1998 catalog," *PBL Biomedical Laboratories*, New Brunswick, New Jersey, Available from: www.interferonsource.com.

PBL, 1999 "Your Total Interferon Source: 1999 catalog," *PBL Biomedical Laboratories*, New Brunswick, New Jersey, Available from: www.interferonsource.com.

PBL, 2000 "Your Total Interferon Source: 2000 catalog," *PBL Biomedical Laboratories*, New Brunswick, New Jersey, Available from: www.interferonsource.com.

Pestka et al., Ann Rev Biochem. 1987;56:727.

Pestka et al., 1983, "Monoclonal Antibodies Can Discriminate between Some Active and Inactive Forms of Leukocyte Interferon," *Archives of Biochemistry and Biophysics*, vol. 224, No. 1: p111-116.

Pogue et al., J. Interferon & Cytokine Research 2004;24:131-139.

Presta, 2003, "Antibody engineering for therapeutics," *Current Opinion of Structural Biology*, vol. 13: p519-525.

Presta, 2005 "Selection, design, and engineering of therapeutic antibodies," *J Allergy Clin Immunol*, vol. 116: p731-736.

Prokunina et al., 2004, "The genetic basis of systemic lupus erythematosus-knowledge of today and thoughts for tomorrow," *Human Molecular Genetics*, vol. 13, Review Issue 1: R143-148.

Prümmer et al., 1989, "Interferon-α Antibodies in Autoimmune Diseases," *Journal of Interferon Research*, vol. 9: Supplement 1: S67-S74.

Prümmer et al., 1994, "Sesitive antiproliferative neutralization assay for the detection of neutralizing IFN-α and IFN-β antibodies," *Journal of Immunological Methods*, vol. 171: p45-53.

Rabinovitch, 1998, "An Update on Cytokines in the Pathogenesis of Insulin-dependent Diabetes Mellitus," *Diabetes/Metabolism Review*, vol. 14: p129-151.

Reddy et al., 2000, "Elimination of Fc Receptor-Dependent Effector Functions of a Modified IgG4 Monoclonal Antibody to Human CD4," *The Journal of Immunology*, vol. 164: p1925-1933 *The Journal of Immunology*, vol. 153: p1360-1377.

Redlich et al., 1991, "Antibodies that neutralize human β interferon biologic activity recognize a linear epitope: Analysis by synthetic peptide mapping," *Proc. Natl. Acad. Sci., USA*, vol. 88: p4040-4044.

Rönnblom et al., 2001, "A Pivotal Role for the Natural Interferon α-producing Cells (Plasmacytoid Dendritic Cells) in the Pathogenesis of Lupus," *J. Exp. Med.*, vol. 194, No. 12: F59-F63.

Rönnblom et al., 2002, "The Natural Inteferon-α Producing Cells in Systemic Lupus Erythematosus," *Human Immunology*, vol. 63: p1181-1193.

Ross et al., 1995, "High Avidity IFN-neutralizing Antibodies in Pharmaceutically Prepared Human IgG," *J. Clin. Invest.*, vol. 95: p1974-1978.

Rudikoff et al. PNAS 198279:1979.

Santiago-Raber; J. Exp. Med 2003;197(6):777-788.

(56) References Cited

OTHER PUBLICATIONS

Santini et al., J Exp Med. 2000;191:1777.
Sattayasai et al., 1988, "Production of Subtype-Specific Antipeptide Antibodies to Human Interferon-α1 and -α4," *Journal of Interferon Research*, vol. 8: p325-332.
Sattayasai et al., 1991, "Subtype-Specificity of Antipeptide Antibodies Raised Against Unique Sequences of Human Interferons- α," *Molecular Immunology*, vol. 28, No. 9: p975-983.
Sattayasai et al., 1991, "Universal Antibodies to Human Interferon-α Subtypes-The Production of Antipeptide Antibodies to Conserved Regions of Interferon-α," *Journal of Interferon Research*, vol. 11: p41-48.
Schmeisser et al., 2002, "Amino Acid Substitutions in Loop BC and Helix C Affect Antigenic Properties of Helix D in Hybrid IFN-α21a/α2c Molecules," *Journal of Interferon and Cytokine Research*, vol. 22: p463-472.
Schmidt et al., 2004, "Targeting interferon-α: a promising approach for systemic lupus erythematosus therapy," *Lupus*, vol. 13: p348-352.
Shearer et al., 1984, "Monoclonal Antibodies That Distinguish Between Subspecies of Human Interferon-α and That Detect Interferon Oligomers," *The Journal of Immunology*, vol. 133, No. 6: p3096-3101.
Somoza et al., 1994, "Pancreas in Recent Onset Insulin-Dependent Diabetes Mellitus,". *The Journal of Immunology*, vol. 153: p1360-1377.
Staehelin et al., 1981, "Production of hybridomas secreting monoclonal antibodies to the human leukocyte interferons," *Proc. Natl. Acad. Sci. USA*, vol. 78, No. 3: p1848-1852.
Staehelin et al., 1981, "Purification and Characterization of Recombinant Human Leukocyte Interferon (IFLrA) with Monoclonal Antibodies," *The Journal of Biological Chemistry*, vol. 256, No. 18: p9750-9754.
Stewart, 2003, "Neutralizing interferon alpha as a therapeutic approach to autoimmune diseases," *Cytokine & Growth Factor Reviews*, vol. 14: p139-154.
Stoll et al. 1996, "Further validation of the BILAG disease activity index in patients with systemic lupus erythematosus," *Ann Rheum Dis*, vol. 55: p756-760.
Tamura et al., "Structural Correlates of an Anticarcinoma Antidoy: Identification of Specificity-Determining Residues (SDRs) and Development of a Minimaly Immunogenic Antibody Variant by Retention of SDRs only", *J. Immunol.*, 164(3): 1432-1441, Feb. 2000.
Taylor-Papadimitriou et al., 1987, "Epitopes of Human Interferon-α Defined by the Reaction of Monoclonal Antibodies with α Interferons and Interferon Analogues," *The Journal of Immunology*, vol. 139, No. 10: p3375-3381.
Thibault et al., 2003, "Interpreting interest in interferon-α," *Arthritis Research & Therapy*, vol. 5, No. 5: p246-248.
Toro et al., 2000, "Detection of Type 1 Cytokines in Discoid Lupus Erythematosus," *Arch Dermatol*, vol. 136: p1497-1501.
Tsukui et al., 1986, "A Monoclonal Antibody with Broad Reactivity to Human Interferon-α Subtypes Useful for Purification of Leukocyte-Derived Interferon," *Microbiol. Immunol.*, vol. 30, No. 11: p1129-1139.
Tsukui et al., 1986, "Two Monoclonal Antibodies Distinguish between Human Recombinant Interferon-α5s Produced by *Escherichia coli* and by Mouse Cells," *Microbiol. Immunol.*, vol. 30, No. 12: p1271-1279.
Uze et al. Cell. 1990;225.
Vallin et al., 1999, "Anti-Double-Stranded DNA Antibodies and Immunostimulatory Plasmid DNA in Combination Mimic the Endogenous IFN-α Inducer in Systemic Lupus Erythematosus," *The Journal of Immunology*, vol. 163: p6306-6313.
Vallin et al., 1999, "Patients with systemic lupus erythematosus (SLE) have a circulating inducer of interferon-alpha (IFN-α) production acting on leucocytes resembling immature dendritic cells," *Clin. Exp. Immunol.*, vol. 115: p196-202.
Vailĉováet al., 2000, "The Carboxyterminal Domains of Human IFN-α2 and IFN-α8 Are Antigenically Homologous," *Journal of Interferon and Cytokine Research*, vol. 20: p455-461.
Viscomi et al., 1999, "Antigenic Characterization of Recombinant, Lymphoblastoid, and Leukocyte IFN-α by Monoclonal Antibodies," *Journal of Interferon and Cytokine Research*, vol. 19: p319-326.
Wang et al., 1994, "Structure-Functioin Analysis of Human IFN-α: Mapping of Conformational Epitope by Homologue Scanning," *Journal of Immunology*, vol. 152: p705-715.
Weissmann et al., 1982, "Structure and expression of human IFN-α genes," *Phil. Trans. R. Soc. Lond. B*, vol. 299: p7-28.
Whittall et al., 1984, "The Reaction of the Anti-interferon-α Monoclonal Antibody, NK2, with Different Interferons," *J gen. Viral.*, vol. 65: p629-633.
Yee et al., 2006, "Revised British Isles Lupus Assessment Group 2004 Index," *Arthritis & Rheumatism*, vol. 54, No. 10: p3300-3305.

Figure 1A

Anti-IFNα 13H5 VH

V segment: 1-18
D segment: undetermined
J segment: JH4b

```
        Q   V   Q   L   V   Q   S   G   A   E   V   K   K   P   G   A   S   V
1       CAG GTT CAG CTG GTG CAG TCT GGA GCT GAG GTG AAG AAG CCT GGG GCC TCA GTG

CDR1 (SEQ ID NO:1)
                                                              --------------------
        K   V   S   C   K   A   S   G   Y   T   F   T   S   Y   S   I   S   W
55      AAG GTC TCC TGC AAG GCT TCT GGT TAC ACC TTT ACC AGC TAT AGT ATC AGC TGG

CDR2
                                                                      --------------
        V   R   Q   A   P   G   Q   G   L   E   W   M   G   W   I   S   V   Y
109     GTG CGA CAG GCC CCT GGA CAA GGG CTT GAG TGG ATG GGA TGG ATC AGC GTT TAC

CDR2 (SEQ ID NO:4)
        ------------------------------------------------
        N   G   N   T   N   Y   A   Q   K   F   Q   G   R   V   T   M   T   T
163     AAT GGT AAC ACA AAC TAT GCA CAG AAG TTC CAG GGC AGA GTC ACC ATG ACC ACA

D   T   S   T   S   T   A   Y   L   E   L   R   S   L   R   S   D   D
217     GAC ACA TCC ACG AGC ACA GCC TAC CTG GAG CTG AGG AGC CTG AGA TCT GAC GAC

CDR3 (SEQ ID NO:7)
                                                   ---------------------
        T   A   V   Y   Y   C   A   R   D   P   I   A   A   G   Y   W   G   Q
271     ACG GCC GTG TAT TAC TGT GCG AGA GAT CCC ATA GCA GCA GGC TAC TGG GGC CAG

G   T   L   V   T   V   S   S           (SEQ ID NO:19)
325     GGA ACC CTG GTC ACC GTC TCC TCA         (SEQ ID NO:25)
```

Figure 1B

Anti-IFNα 13H5 VK

V segment: A27
J segment: JK1

```
          E   I   V   L   T   Q   S   P   G   T   L   S   L   S   P   G   E   R
  1       GAA ATT GTG TTG ACG CAG TCT CCA GGC ACC CTG TCT TTG TCT CCA GGG GAA AGA

CDR1 (SEQ ID NO:10)
                                              ----------------------------------
          A   T   L   S   C   R   A   S   Q   S   V   S   S   T   Y   L   A   W
 55       GCC ACC CTC TCC TGC AGG GCC AGT CAG AGT GTT AGC AGC ACC TAC TTA GCC TGG

CDR2
                                                                         --------
          Y   Q   Q   K   P   G   Q   A   P   R   L   L   I   Y   G   A   S
109       TAC CAG CAG AAA CCT GGC CAG GCT CCC AGG CTC CTC ATC TAT GGT GCA TCC AGC

CDR2 (SEQ ID NO:13)
              -----------
          R   A   T   G   I   P   D   R   F   S   G   S   G   S   G   T   D   F
163       AGG GCC ACT GGC ATC CCA GAC AGG TTC AGT GGC AGT GGG TCT GGG ACA GAC TTC

---
          T   L   T   I   S   R   L   E   P   E   D   F   A   V   Y   Y   C   Q
217       ACT CTC ACC ATC AGC AGA CTG GAG CCT GAA GAT TTT GCA GTG TAT TAC TGT CAG

CDR3 (SEQ ID NO:16)
              ------------------------------            (SEQ ID NO:22)
          Q   Y   G   S   S   P   R   T   F   G   Q   G   T   K   V   E   I   K
271       CAG TAT GGT AGC TCA CCT CGG ACG TTC GGC CAA GGG ACC AAG GTG GAA ATC AAA
                                                            (SEQ ID NO:28)
```

Figure 2A

Anti-IFNα 13H7 VH

```
V segment:    4-61
D segment:    3-10
J segment:    JH4b
```

```
        Q   V   Q   L   Q   E   S   G   P   G   L   M   K   P   S   E   T   L
  1     CAG GTG CAG CTG CAG GAG TCG GGC CCA GGA CTG ATG AAG CCT TCG GAG ACC CTG

CDR1 (SEQ ID NO:2)
                                                              ---------------------
        S   L   T   C   T   V   S   G   G   S   V   S   S   G   S   Y   Y   W
 55     TCC CTC ACC TGC ACT GTC TCT GGT GGC TCC GTC AGC AGT GGT AGT TAC TAC TGG

----
        S   W   I   R   Q   P   P   G   M   G   L   E   W   I   G   Y   I   Y
109     AGC TGG ATC CGG CAG CCC CCA GGG ATG GGA CTG GAG TGG ATT GGT TAT ATC TAT

CDR2 (SEQ ID NO:5)
                          --------------------------------------------------
        S   G   G   G   A   N   Y   N   P   S   L   K   S   R   V   T   I   S
163     TCC GGG GGA GGC GCC AAC TAC AAC CCT TCC CTC AAG AGT CGA GTC ACC ATA TCA

V   D   T   S   K   N   Q   F   S   L   K   L   N   S   V   T   A   A
217     GTG GAC ACG TCC AAG AAC CAG TTC TCC CTG AAG CTG AAC TCT GTG ACC GCT GCG

CDR3 (SEQ ID NO:8)
                                                              ---------------------
        D   T   A   V   Y   F   C   A   R   G   I   P   M   V   R   G   I   L
271     GAC ACG GCC GTG TAT TTC TGT GCG AGA GGA ATT CCT ATG GTT CGG GGA ATT CTT

-----------
        H   Y   W   G   Q   G   T   L   V   T   V   S   S       (SEQ ID NO:20)
325     CAC TAC TGG GGC CAG GGA ACC CTG GTC ACC GTC TCC TCA      (SEQ ID NO:26)
```

Figure 2B

Anti-IFNα 13H7 VK

V segment:    A27
J segment:    JK2

```
        E   I   V   L   T   Q   S   P   G   T   L   S   L   S   P   G   E   R
  1    GAA ATT GTG TTG ACG CAG TCT CCA GGC ACC CTG TCT TTG TCT CCA GGG GAA AGA
```
                                                  CDR1 (SEQ ID NO:11)
                                        ------------------------------------------
```
        A   T   L   S   C   R   A   S   Q   S   V   S   S   S   F   L   A   W
 55    GCC ACC CTC TCC TGC AGG GCC AGT CAG AGT GTT AGC AGC AGC TTC TTA GCC TGG
```
                                                                          CDR2
                                                                  ------------------
```
        Y   Q   Q   K   P   G   Q   A   P   R   L   L   I   Y   G   A   S   S
109    TAC CAG CAG AAA CCT GGC CAG GCT CCC AGG CTC CTC ATC TAT GGT GCA TCC AGC
```
        CDR2 (SEQ ID NO:14)
  ------------------
```
        R   A   T   G   I   P   D   R   F   S   G   S   G   S   G   T   D   F
163    AGG GCC ACT GGC ATC CCA GAC AGG TTC AGT GGC AGT GGG TCT GGG ACA GAC TTC

CDR3
                                                                             ---
        T   L   T   I   S   R   L   E   P   E   D   F   A   V   Y   Y   C   Q
217    ACT CTC ACC ATC AGC AGA CTG GAG CCT GAA GAT TTT GCA GTG TAT TAC TGT CAG
```
              CDR3 (SEQ ID NO:17)
        ----------------------------------                         (SEQ ID NO:23)
```
        Q   Y   G   S   S   P   Y   T   F   G   Q   G   T   K   L   E   I   K
271    CAG TAT GGT AGC TCA CCG TAC ACT TTT GGC CAG GGG ACC AAG CTG GAG ATC AAA
                                                                 (SEQ ID NO:29)
```

Figure 3A

Anti-Interferon α 7H9 VH

V segment:  1-18
    D segment:  6-6
    J segment:  JH4b

```
         Q   V   Q   L   V   Q   S   G   A   E   V   K   K   P   G   A   S   V
  1      CAG GTT CAG CTG GTG CAG TCT GGA GCT GAG GTG AAG AAG CCT GGG GCC TCA GTG

CDR1 (SEQ ID NO:3)
                                                              ---------------------
         K   V   S   C   K   A   S   G   Y   T   F   S   S   Y   G   I   S   W
  55     AAG GTC TCC TGC AAG GCT TCT GGT TAT ACC TTT TCC AGC TAT GGT ATC AGC TGG

CDR2
                                                                     ---------------
         V   R   Q   A   P   G   Q   G   L   E   W   M   G   W   I   S   A   Y
  109    GTG CGA CAG GCC CCT GGA CAA GGA CTT GAG TGG ATG GGA TGG ATC AGC GCT TAC

CDR2 (SEQ ID NO:6)
         ----------------------------------------
         N   G   N   T   N   Y   L   Q   K   L   Q   G   R   V   T   L   T   T
  163    AAT GGT AAC ACA AAC TAT CTA CAG AAG CTC CAG GGC AGA GTC ACC CTG ACC ACA

D   T   S   T   N   T   A   Y   M   E   L   R   S   L   R   S   D   D
  217    GAC ACA TCC ACG AAC ACA GCC TAC ATG GAG CTG AGG AGC CTG AGA TCT GAC GAC

CDR3 (SEQ ID NO:9)
                                                              ---------------------
         T   A   V   Y   Y   C   T   R   D   P   I   A   A   G   Y   W   G   Q
  271    ACG GCC GTG TAT TAC TGT ACG AGA GAT CCC ATA GCA GCA GGT TAC TGG GGC CAG

G   T   L   V   T   V   S   S          (SEQ ID NO:21)
  325    GGA ACC CTG GTC ACC GTC TCC TCA        (SEQ ID NO:27)
```

Figure 3B

Anti-Interferon α 7H9 VK

V segment: A27
J segment: JK1

```
         E   I   V   L   T   Q   S   P   G   T   L   S   L   S   P   G   E   R
  1      GAA ATT GTG TTG ACG CAG TCT CCA GGC ACC CTG TCT TTG TCT CCA GGG GAA AGA

CDR1 (SEQ ID NO:12)
                                    ------------------------------------------------
         A   T   L   S   C   R   A   S   Q   S   V   S   S   T   Y   L   A   W
  55     GCC ACC CTC TCC TGC AGG GCC AGT CAG AGT GTT AGC AGC ACC TAC TTA GCC TGG

CDR2
                                                                          -----------------
         Y   Q   Q   K   P   G   Q   A   P   R   L   L   I   Y   G   A   S   S
 109     TAC CAG CAG AAA CCT GGC CAG GCT CCC AGG CTC CTC ATC TAT GGT GCA TCC AGC

CDR2 (SEQ ID NO:15)
         --------------------
         R   A   T   G   I   P   D   R   F   S   G   S   G   S   G   T   D   F
 163     AGG GCC ACT GGC ATC CCA GAC AGG TTC AGT GGC AGT GGG TCT GGG ACA GAC TTC

CDR3
                                                                              ---
         T   L   T   I   S   R   L   E   P   E   D   F   A   V   Y   Y   C   Q
 217     ACT CTC ACC ATC AGC AGA CTG GAG CCT GAA GAT TTT GCA GTG TAT TAC TGT CAG

CDR3 (SEQ ID NO:18)
         ------------------------------------            (SEQ ID NO:24)
         Q   Y   G   S   S   P   R   T   F   G   Q   G   T   K   V   E   I   K
 271     CAG TAT GGT AGC TCA CCT CGG ACG TTC GGC CAA GGG ACC AAG GTG GAA ATC AAA
                                                                  (SEQ ID NO:30)
```

Anti-IFNα V_H region

```
                      CDR1
1-18 Germline:  Q V Q L V Q S G A E V K K P G A S V K V S C K A S G Y T F T S Y G I S W V R Q
13H5 V_H:       - - - - - - - - - - - - - - - - - - - - - - - - - - - - S - - - S - - - - -
7H9 VH:         - - - - - - - - - - - - - - - - - - - - - - - - - - - - - - - - - - - - - -

CDR2
1-18 Germline:  A P G Q G L E W M G W I S A Y N G N T N Y A Q K L Q G R V T M T T D T S T S T
13H5 V_H:       - - - - - - - - - - - - - - V - - - - - - - L - - - P - - - - - - - - - - -
7H9 VH:         - - - - - - - - - - - - - - - - - - - - - - - - - - - - - L - - - - - - - N (SEQ ID NO:31)                        CDR3
1-18 Germline:  A Y M E L R S L R S D D T A V Y Y C A R - - - D P I A A G Y W G Q G T L V T V S S  (JH4b)
13H5 V_H:       - - - - - L - - - - - - - - - - - - - - - - - - - - - - - - - - - - - - - - -
7H9 VH:         - - - - - - - - - - - - - - - - - - - - T - - - - - - - - - - - - - - - - - -  (JH4b)
```

Figure 4

Anti-IFNα V_H Region

```
                                                            CDR1
4-61 Germline:  Q V Q L Q E S G P G L V K P S E T L S L T C T V S G G S V S S G G Y Y W S W I R Q P
13H7 VH:        - - - - - - - - - - - - - - - M - - - - - - - - - - - - - - - - - - - - - - - -

CDR2
4-61 Germline:  P G K G L E W I G Y I Y Y S G S T N Y N P S L K S R V T I S V D T S K N Q F S L K L
13H7 VH:        - - - M - - - - - - - - - S G - G A - - - - - - - - - - - - - - - - - - - - - - -

(SEQ ID NO:32)              CDR3
4-61 Germline:  S S V T A A D T A V Y Y C A R
13H7 VH:        - - - - - - - - - - - - - - - F - - G I P M V R G I L H Y W G Q G T L V T V S S  (JH4b)
                N - -
```

Figure 5

Anti-IFNα V<sub>K</sub> Region

```
                                                            CDR1
A27 Germline:  E I V L T Q S P G T L S L S P G E R A T L S C R A S Q S V S S S Y L A
13H5 VK:       - - - - - - - - - - - - - - - - - - - - - - - - - - - - - T - - -
7H9 VK:        - - - - - - - - - - - - - - - - - - - - - - - - - - - - - T - - -
13H7 VK:       - - - - - - - - - - - - - - - - - - - - - - - - - - - - - - - - F CDR2
A27 Germline:  W Y Q Q K P G Q A P R L L I Y G A S S R A T G I P D R F S G S G S G T
13H5 VK:       - - - - - - - - - - - - - - - - - - - - - - - - - - - - - - - - -
7H9 VK:        - - - - - - - - - - - - - - - - - - - - - - - - - - - - - - - - -
13H7 VK:       - - - - - - - - - - - - - - - - - - - - - - - - - - - - - - - - -

CDR3
A27 Germline:  D F T L T I S R L E P E D F A V Y Y C Q Q Y G S S P       R T F G Q G T K V E I K  (JK1)
                                           (SEQ ID NO:33)
13H5 VK:       - - - - - - - - - - - - - - - - - - - - - - - -         - - - - - - - - - - -    (JK1)
7H9 VK:        - - - - - - - - - - - - - - - - - - - - - - Y -         - - - - - - - - L - -    (JK2)
13H7 VK:       - - - - - - - - - - - - - - - - - - - - - - - -         - - - - - - - - - - -
```

Figure 6

```
                           SEQUENCE LISTING

<160> NUMBER OF SEQ ID NOS: 41

<210> SEQ ID NO 1
<211> LENGTH: 5
<212> TYPE: PRT
<213> ORGANISM: Homo sapiens

<400> SEQUENCE: 1

Ser Tyr Ser Ile Ser
1               5

<210> SEQ ID NO 2
<211> LENGTH: 7
<212> TYPE: PRT
<213> ORGANISM: Homo sapiens

<400> SEQUENCE: 2

Ser Gly Ser Tyr Tyr Trp Ser
1               5

<210> SEQ ID NO 3
<211> LENGTH: 5
<212> TYPE: PRT
<213> ORGANISM: Homo sapiens

<400> SEQUENCE: 3

Ser Tyr Gly Ile Ser
1               5

<210> SEQ ID NO 4
<211> LENGTH: 17
<212> TYPE: PRT
<213> ORGANISM: Homo sapiens
```

-continued

```
<400> SEQUENCE: 4

Trp Ile Ser Val Tyr Asn Gly Asn Thr Asn Tyr Ala Gln Lys Phe Gln
1               5                   10                  15
Gly

<210> SEQ ID NO 5
<211> LENGTH: 16
<212> TYPE: PRT
<213> ORGANISM: Homo sapiens

<400> SEQUENCE: 5

Tyr Ile Tyr Ser Gly Gly Gly Ala Asn Tyr Asn Pro Ser Leu Lys Ser
1               5                   10                  15

<210> SEQ ID NO 6
<211> LENGTH: 17
<212> TYPE: PRT
<213> ORGANISM: Homo sapiens

<400> SEQUENCE: 6

Trp Ile Ser Ala Tyr Asn Gly Asn Thr Asn Tyr Leu Gln Lys Leu Gln
1               5                   10                  15
Gly

<210> SEQ ID NO 7
<211> LENGTH: 7
<212> TYPE: PRT
<213> ORGANISM: Homo sapiens

<400> SEQUENCE: 7

Asp Pro Ile Ala Ala Gly Tyr
1               5

<210> SEQ ID NO 8
<211> LENGTH: 11
<212> TYPE: PRT
<213> ORGANISM: Homo sapiens

<400> SEQUENCE: 8

Gly Ile Pro Met Val Arg Gly Ile Leu His Tyr
1               5                   10

<210> SEQ ID NO 9
<211> LENGTH: 7
<212> TYPE: PRT
<213> ORGANISM: Homo sapiens

<400> SEQUENCE: 9

Asp Pro Ile Ala Ala Gly Tyr
1               5

<210> SEQ ID NO 10
<211> LENGTH: 12
<212> TYPE: PRT
<213> ORGANISM: Homo sapiens

<400> SEQUENCE: 10

Arg Ala Ser Gln Ser Val Ser Ser Thr Tyr Leu Ala
1               5                   10

<210> SEQ ID NO 11
<211> LENGTH: 12
<212> TYPE: PRT
<213> ORGANISM: Homo sapiens
```

<400> SEQUENCE: 11

Arg Ala Ser Gln Ser Val Ser Ser Ser Phe Leu Ala
 1               5                  10

<210> SEQ ID NO 12
<211> LENGTH: 12
<212> TYPE: PRT
<213> ORGANISM: Homo sapiens

<400> SEQUENCE: 12

Arg Ala Ser Gln Ser Val Ser Ser Thr Tyr Leu Ala
 1               5                  10

<210> SEQ ID NO 13
<211> LENGTH: 7
<212> TYPE: PRT
<213> ORGANISM: Homo sapiens

<400> SEQUENCE: 13

Gly Ala Ser Ser Arg Ala Thr
 1               5

<210> SEQ ID NO 14
<211> LENGTH: 7
<212> TYPE: PRT
<213> ORGANISM: Homo sapiens

<400> SEQUENCE: 14

Gly Ala Ser Ser Arg Ala Thr
 1               5

<210> SEQ ID NO 15
<211> LENGTH: 7
<212> TYPE: PRT
<213> ORGANISM: Homo sapiens

<400> SEQUENCE: 15

Gly Ala Ser Ser Arg Ala Thr
 1               5

<210> SEQ ID NO 16
<211> LENGTH: 9
<212> TYPE: PRT
<213> ORGANISM: Homo sapiens

<400> SEQUENCE: 16

Gln Gln Tyr Gly Ser Ser Pro Arg Thr
 1               5

<210> SEQ ID NO 17
<211> LENGTH: 9
<212> TYPE: PRT
<213> ORGANISM: Homo sapiens

<400> SEQUENCE: 17

Gln Gln Tyr Gly Ser Ser Pro Tyr Thr
 1               5

<210> SEQ ID NO 18
<211> LENGTH: 9
<212> TYPE: PRT
<213> ORGANISM: Homo sapiens

```
<400> SEQUENCE: 18

Gln Gln Tyr Gly Ser Ser Pro Arg Thr
  1               5

<210> SEQ ID NO 19
<211> LENGTH: 116
<212> TYPE: PRT
<213> ORGANISM: Homo sapiens

<400> SEQUENCE: 19

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Ser Ile Ser Trp Val Arg Gln Ala Pro Gly Gln Gly Leu Glu Trp Met
             35                  40                  45

Gly Trp Ile Ser Val Tyr Asn Gly Asn Thr Asn Tyr Ala Gln Lys Phe
         50                  55                  60

Gln Gly Arg Val Thr Met Thr Thr Asp Thr Ser Thr Ser Thr Ala Tyr
 65                  70                  75                  80

Leu Glu Leu Arg Ser Leu Arg Ser Asp Asp Thr Ala Val Tyr Tyr Cys
                 85                  90                  95

Ala Arg Asp Pro Ile Ala Ala Gly Tyr Trp Gly Gln Gly Thr Leu Val
            100                 105                 110

Thr Val Ser Ser
        115

<210> SEQ ID NO 20
<211> LENGTH: 121
<212> TYPE: PRT
<213> ORGANISM: Homo sapiens

<400> SEQUENCE: 20

Gln Val Gln Leu Gln Glu Ser Gly Pro Gly Leu Met Lys Pro Ser Glu
  1               5                  10                  15

Thr Leu Ser Leu Thr Cys Thr Val Ser Gly Gly Ser Val Ser Ser Gly
                 20                  25                  30

Ser Tyr Tyr Trp Ser Trp Ile Arg Gln Pro Pro Gly Met Gly Leu Glu
             35                  40                  45

Trp Ile Gly Tyr Ile Tyr Ser Gly Gly Ala Asn Tyr Asn Pro Ser
         50                  55                  60

Leu Lys Ser Arg Val Thr Ile Ser Val Asp Thr Ser Lys Asn Gln Phe
 65                  70                  75                  80

Ser Leu Lys Leu Asn Ser Val Thr Ala Ala Asp Thr Ala Val Tyr Phe
                 85                  90                  95

Cys Ala Arg Gly Ile Pro Met Val Arg Gly Ile Leu His Tyr Trp Gly
            100                 105                 110

Gln Gly Thr Leu Val Thr Val Ser Ser
            115                 120

<210> SEQ ID NO 21
<211> LENGTH: 116
<212> TYPE: PRT
<213> ORGANISM: Homo sapiens
```

<400> SEQUENCE: 21

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Leu Gln Lys Leu
        50                  55                  60

Gln Gly Arg Val Thr Leu Thr Thr Asp Thr Ser Thr Asn Thr Ala Tyr
 65                  70                  75                  80

Met Glu Leu Arg Ser Leu Arg Ser Asp Asp Thr Ala Val Tyr Tyr Cys
                85                  90                  95

Thr Arg Asp Pro Ile Ala Ala Gly Tyr Trp Gly Gln Gly Thr Leu Val
            100                 105                 110

Thr Val Ser Ser
        115

<210> SEQ ID NO 22
<211> LENGTH: 108
<212> TYPE: PRT
<213> ORGANISM: Homo sapiens

<400> SEQUENCE: 22

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Thr
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys
            100                 105

<210> SEQ ID NO 23
<211> LENGTH: 108
<212> TYPE: PRT
<213> ORGANISM: Homo sapiens

<400> SEQUENCE: 23

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

```
Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105
```

<210> SEQ ID NO 24
<211> LENGTH: 108
<212> TYPE: PRT
<213> ORGANISM: Homo sapiens

<400> SEQUENCE: 24

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Thr
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys
            100                 105
```

<210> SEQ ID NO 25
<211> LENGTH: 348
<212> TYPE: DNA
<213> ORGANISM: Homo sapiens
<220> FEATURE:
<221> NAME/KEY: CDS
<222> LOCATION: (1)..(348)

<400> SEQUENCE: 25

```
cag gtt cag ctg gtg cag tct gga gct gag gtg aag aag cct ggg gcc     48
Gln Val Gln Leu Val Gln Ser Gly Ala Glu Val Lys Lys Pro Gly Ala
  1               5                  10                  15 tca gtg aag gtc tcc tgc aag gct tct ggt tac acc ttt acc agc tat     96
Ser Val Lys Val Ser Cys Lys Ala Ser Gly Tyr Thr Phe Thr Ser Tyr
             20                  25                  30 agt atc agc tgg gtg cga cag gcc cct gga caa ggg ctt gag tgg atg    144
Ser Ile Ser Trp Val Arg Gln Ala Pro Gly Gln Gly Leu Glu Trp Met
         35                  40                  45 gga tgg atc agc gtt tac aat ggt aac aca aac tat gca cag aag ttc    192
Gly Trp Ile Ser Val Tyr Asn Gly Asn Thr Asn Tyr Ala Gln Lys Phe
 50                  55                  60 cag ggc aga gtc acc atg acc aca gac aca tcc acg agc aca gcc tac    240
Gln Gly Arg Val Thr Met Thr Thr Asp Thr Ser Thr Ser Thr Ala Tyr
 65                  70                  75                  80 ctg gag ctg agg agc ctg aga tct gac gac acg gcc gtg tat tac tgt    288
Leu Glu Leu Arg Ser Leu Arg Ser Asp Asp Thr Ala Val Tyr Tyr Cys
                85                  90                  95 gcg aga gat ccc ata gca gca ggc tac tgg ggc cag gga acc ctg gtc    336
Ala Arg Asp Pro Ile Ala Ala Gly Tyr Trp Gly Gln Gly Thr Leu Val
            100                 105                 110 acc gtc tcc tca                                                    348
Thr Val Ser Ser
            115
```

<210> SEQ ID NO 26
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 26

```
cag gtg cag ctg cag gag tcg ggc cca gga ctg atg aag cct tcg gag        48
Gln Val Gln Leu Gln Glu Ser Gly Pro Gly Leu Met Lys Pro Ser Glu
 1               5                  10                  15 acc ctg tcc ctc acc tgc act gtc tct ggt ggc tcc gtc agc agt ggt        96
Thr Leu Ser Leu Thr Cys Thr Val Ser Gly Gly Ser Val Ser Ser Gly
             20                  25                  30 agt tac tac tgg agc tgg atc cgg cag ccc cca ggg atg gga ctg gag       144
Ser Tyr Tyr Trp Ser Trp Ile Arg Gln Pro Pro Gly Met Gly Leu Glu
         35                  40                  45 tgg att ggt tat atc tat tcc ggg gga ggc gcc aac tac aac cct tcc       192
Trp Ile Gly Tyr Ile Tyr Ser Gly Gly Gly Ala Asn Tyr Asn Pro Ser
     50                  55                  60 ctc aag agt cga gtc acc ata tca gtg gac acg tcc aag aac cag ttc       240
Leu Lys Ser Arg Val Thr Ile Ser Val Asp Thr Ser Lys Asn Gln Phe
 65                  70                  75                  80 tcc ctg aag ctg aac tct gtg acc gct gcg gac acg gcc gtg tat ttc       288
Ser Leu Lys Leu Asn Ser Val Thr Ala Ala Asp Thr Ala Val Tyr Phe
                 85                  90                  95 tgt gcg aga gga att cct atg gtt cgg gga att ctt cac tac tgg ggc       336
Cys Ala Arg Gly Ile Pro Met Val Arg Gly Ile Leu His Tyr Trp Gly
            100                 105                 110 cag gga acc ctg gtc acc gtc tcc tca                                   363
Gln Gly Thr Leu Val Thr Val Ser Ser
        115                 120
```

<210> SEQ ID NO 27
<211> LENGTH: 348
<212> TYPE: DNA
<213> ORGANISM: Homo sapiens
<220> FEATURE:
<221> NAME/KEY: CDS
<222> LOCATION: (1)..(348)

<400> SEQUENCE: 27

```
cag gtt cag ctg gtg cag tct gga gct gag gtg aag aag cct ggg gcc        48
Gln Val Gln Leu Val Gln Ser Gly Ala Glu Val Lys Lys Pro Gly Ala
 1               5                  10                  15 tca gtg aag gtc tcc tgc aag gct tct ggt tat acc ttt tcc agc tat        96
Ser Val Lys Val Ser Cys Lys Ala Ser Gly Tyr Thr Phe Ser Ser Tyr
             20                  25                  30 ggt atc agc tgg gtg cga cag gcc cct gga caa gga ctt gag tgg atg       144
Gly Ile Ser Trp Val Arg Gln Ala Pro Gly Gln Gly Leu Glu Trp Met
         35                  40                  45 gga tgg atc agc gct tac aat ggt aac aca aac tat cta cag aag ctc       192
Gly Trp Ile Ser Ala Tyr Asn Gly Asn Thr Asn Tyr Leu Gln Lys Leu
     50                  55                  60 cag ggc aga gtc acc ctg acc aca gac aca tcc acg aac aca gcc tac       240
Gln Gly Arg Val Thr Leu Thr Thr Asp Thr Ser Thr Asn Thr Ala Tyr
 65                  70                  75                  80 atg gag ctg agg agc ctg aga tct gac gac acg gcc gtg tat tac tgt       288
Met Glu Leu Arg Ser Leu Arg Ser Asp Asp Thr Ala Val Tyr Tyr Cys
                 85                  90                  95
```

```
acg aga gat ccc ata gca gca ggt tac tgg ggc cag gga acc ctg gtc      336
Thr Arg Asp Pro Ile Ala Ala Gly Tyr Trp Gly Gln Gly Thr Leu Val
        100                 105                 110 acc gtc tcc tca                                                      348
Thr Val Ser Ser
        115

<210> SEQ ID NO 28
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 28 gaa att gtg ttg acg cag tct cca ggc acc ctg tct ttg tct cca ggg       48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc acc       96
Glu Arg Ala Thr Leu Ser Cys Arg Ala Ser Gln Ser Val Ser Ser Thr
            20                  25                  30 tac tta gcc tgg tac cag cag aaa cct ggc cag gct ccc agg ctc ctc      144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt      192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag      240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agc tca cct      288
Pro Glu Asp Phe Ala Val Tyr Tyr Cys Gln Gln Tyr Gly Ser Ser Pro
                85                  90                  95 cgg acg ttc ggc caa ggg acc aag gtg gaa atc aaa                      324
Arg Thr Phe Gly Gln Gly Thr Lys Val Glu Ile Lys
            100                 105

<210> SEQ ID NO 29
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 29 gaa att gtg ttg acg cag tct cca ggc acc ctg tct ttg tct cca ggg       48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc       96
Glu Arg Ala Thr Leu Ser Cys Arg Ala Ser Gln Ser Val Ser Ser Ser
            20                  25                  30 ttc tta gcc tgg tac cag cag aaa cct ggc cag gct ccc agg ctc ctc      144
Phe Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt      192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag      240
Gly Ser Gly Ser Gly Thr Asp Phe Thr Leu Thr Ile Ser Arg Leu Glu
65                  70                  75                  80
```

```
cct gaa gat ttt gca gtg tat tac tgt cag cag tat ggt agc tca ccg     288
Pro Glu Asp Phe Ala Val Tyr Tyr Cys Gln Gln Tyr Gly Ser Ser Pro
             85                  90                  95 tac act ttt ggc cag ggg acc aag ctg gag atc aaa                     324
Tyr Thr Phe Gly Gln Gly Thr Lys Leu Glu Ile Lys
        100                 105

<210> SEQ ID NO 30
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 30 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
  1               5                  10                  15 gaa aga gcc acc ctc tcc tgc agg gcc agt cag agt gtt agc agc acc      96
Glu Arg Ala Thr Leu Ser Cys Arg Ala Ser Gln Ser Val Ser Ser Thr
             20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
         35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
     50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat ggt agc tca cct     288
Pro Glu Asp Phe Ala Val Tyr Tyr Cys Gln Gln Tyr Gly Ser Ser Pro
             85                  90                  95 cgg acg ttc ggc caa ggg acc aag gtg gaa atc aaa                     324
Arg Thr Phe Gly Gln Gly Thr Lys Val Glu Ile Lys
        100                 105

<210> SEQ ID NO 31
<211> LENGTH: 98
<212> TYPE: PRT
<213> ORGANISM: Homo sapiens

<400> SEQUENCE: 31

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Gly Ile Ser Trp Val Arg Gln Ala Pro Gly Gln Gly Leu Glu Trp Met
         35                  40                  45

Gly Trp Ile Ser Ala Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
             85                  90                  95

Ala Arg

<210> SEQ ID NO 32
<211> LENGTH: 99
<212> TYPE: PRT
<213> ORGANISM: Homo sapiens
```

<400> SEQUENCE: 32

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
 50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 33
<211> LENGTH: 96
<212> TYPE: PRT
<213> ORGANISM: Homo sapiens

<400> SEQUENCE: 33

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 34
<211> LENGTH: 116
<212> TYPE: PRT
<213> ORGANISM: Homo sapiens

<400> SEQUENCE: 34

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Ser Ile Ser Trp Val Arg Gln Ala Pro Gly Gln Gly Leu Glu Trp Met
        35                  40                  45

Gly Trp Ile Ser Val Tyr Asp Gly Asn Thr Asn Tyr Ala Gln Lys Phe
 50                  55                  60

Gln Gly Arg Val Thr Met Thr Thr Asp Thr Ser Thr Ser Thr Ala Tyr
65                  70                  75                  80

Leu Glu Leu Arg Ser Leu Arg Ser Asp Asp Thr Ala Val Tyr Tyr Cys
                85                  90                  95

Ala Arg Asp Pro Ile Ala Ala Gly Tyr Trp Gly Gln Gly Thr Leu Val
            100                 105                 110

Thr Val Ser Ser
        115

```
<210> SEQ ID NO 35
<211> LENGTH: 116
<212> TYPE: PRT
<213> ORGANISM: Homo sapiens

<400> SEQUENCE: 35

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Ser Ile Ser Trp Val Arg Gln Ala Pro Gly Gln Gly Leu Glu Trp Met
         35                  40                  45

Gly Trp Ile Ser Val Tyr Gln Gly Asn Thr Asn Tyr Ala Gln Lys Phe
     50                  55                  60

Gln Gly Arg Val Thr Met Thr Thr Asp Thr Ser Thr Ser Thr Ala Tyr
 65                  70                  75                  80

Leu Glu Leu Arg Ser Leu Arg Ser Asp Asp Thr Ala Val Tyr Tyr Cys
                 85                  90                  95

Ala Arg Asp Pro Ile Ala Ala Gly Tyr Trp Gly Gln Gly Thr Leu Val
             100                 105                 110

Thr Val Ser Ser
        115

<210> SEQ ID NO 36
<211> LENGTH: 116
<212> TYPE: PRT
<213> ORGANISM: Homo sapiens

<400> SEQUENCE: 36

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Ser Ile Ser Trp Val Arg Gln Ala Pro Gly Gln Gly Leu Glu Trp Met
         35                  40                  45

Gly Trp Ile Ser Val Tyr Gln Gly Gln Thr Asn Tyr Ala Gln Lys Phe
     50                  55                  60

Gln Gly Arg Val Thr Met Thr Thr Asp Thr Ser Thr Ser Thr Ala Tyr
 65                  70                  75                  80

Leu Glu Leu Arg Ser Leu Arg Ser Asp Asp Thr Ala Val Tyr Tyr Cys
                 85                  90                  95

Ala Arg Asp Pro Ile Ala Ala Gly Tyr Trp Gly Gln Gly Thr Leu Val
             100                 105                 110

Thr Val Ser Ser
        115

<210> SEQ ID NO 37
<211> LENGTH: 116
<212> TYPE: PRT
<213> ORGANISM: Homo sapiens

<400> SEQUENCE: 37

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Ser Ile Ser Trp Val Arg Gln Ala Pro Gly Gln Gly Leu Glu Trp Met
         35                  40                  45
```

```
Gly Trp Ile Ser Val Tyr Asn Ala Asn Thr Asn Tyr Ala Gln Lys Phe
     50                  55                  60

Gln Gly Arg Val Thr Met Thr Thr Asp Thr Ser Thr Ser Thr Ala Tyr
 65              70                  75                  80

Leu Glu Leu Arg Ser Leu Arg Ser Asp Thr Ala Val Tyr Tyr Cys
                 85                  90                  95

Ala Arg Asp Pro Ile Ala Ala Gly Tyr Trp Gly Gln Gly Thr Leu Val
             100                 105                 110

Thr Val Ser Ser
        115

<210> SEQ ID NO 38
<211> LENGTH: 4
<212> TYPE: PRT
<213> ORGANISM: Homo sapiens

<400> SEQUENCE: 38

Asp Gly Asn Thr
 1

<210> SEQ ID NO 39
<211> LENGTH: 4
<212> TYPE: PRT
<213> ORGANISM: Homo sapiens

<400> SEQUENCE: 39

Gln Gly Asn Thr
 1

<210> SEQ ID NO 40
<211> LENGTH: 4
<212> TYPE: PRT
<213> ORGANISM: Homo sapiens

<400> SEQUENCE: 40

Gln Gly Gln Thr
 1

<210> SEQ ID NO 41
<211> LENGTH: 4
<212> TYPE: PRT
<213> ORGANISM: Homo sapiens

<400> SEQUENCE: 41

Asn Gly Asn Thr
 1
```

NUCLEIC ACIDS ENCODING INTERFERON ALPHA ANTIBODIES

CROSS REFERENCE TO RELATED APPLICATIONS

This application is a continuation application of U.S. application Ser. No. 13/211,092, filed Aug. 16, 2011, which is a continuation application of U.S. application Ser. No. 12/551,250, filed Aug. 31, 2009, now U.S. Pat. No. 8,025,882, which is a divisional application of U.S. application Ser. No. 11/009,410, filed Dec. 10, 2004, now U.S. Pat. No. 7,741,449, which claims priority to U.S. Provisional Ser. No. 60/528,757, filed Dec. 10, 2003, the contents of each of which are incorporated by reference in their entirety.

SEQUENCE LISTING

The specification further incorporates by reference the Sequence Listing submitted via EFS on Jun. 4, 2011. The Sequence Listing text file, identified as 077375.0963SEQLIST.txt, is 27,610 bytes and was created Jun. 3, 2013. The Sequence Listing, electronically filed, does not extend beyond the scope of the specification and does not contain new matter.

BACKGROUND OF THE INVENTION

Type I interferons (IFN) IFN-α, IFN-β, IFN-Ω, IFN-τ) are a family of structurally related cytokines having antiviral, antitumor and immunomodulatory effects (Hardy et al. (2001) *Blood* 97:473; Cutrone and Langer (2001) *J. Biol. Chem.* 276:17140). The human IFNα locus includes two subfamilies. The first subfamily consists of at least 14 non allelic genes and 4 pseudogenes having at least 75% homology. The second subfamily, αII or omega (Ω), contains 5 pseudogenes and 1 functional gene which exhibits 70% homology with the IFNα genes. The subtypes of IFNα have different specific activities but they possess the same biological spectrum (Streuli et al. (1981) *Proc. Natl. Acad. Sci. USA* 78:2848) and have the same cellular receptor (Agnet M. et al. (1983) in "Interferon 5" Ed. I. Gresser p. 1-22, Academic Press, London).

All human type I interferons bind to a cell surface receptor (IFN alpha receptor, IFNAR) consisting of two transmembrane proteins, IFNAR-1 and IFNAR-2 (Uze et. al. (1990) *Cell* 60:225; Novick et al. (1994) *Cell* 77:391; Pestka et al. (1987) *Annu Rev. Biochem.* 56:727; Mogensen et al. (1999) *J. Interferon Cytokine Res.* 19:1069), IFNAR-1 is essential for high affinity binding and differential specificity of the IFNAR complex (Cutrone (2001) supra). While functional differences for each of the type I IFN subtypes have not been identified it is thought that each may exhibit different interactions with the IFNAR receptor components leading to potentially diverse signaling outcomes (Cook et al. (1996) *J. Biol. Chem.* 271:13448). In particular, studies utilizing mutant forms of IFNAR1 and IFNAR2 suggested that alpha and beta interferons signal differently through the receptor by interacting differentially with respective chains (Lewerenz et al. (1998) *J. Mol. Biol.* 282:585).

Early functional studies of type I IFNs focused on innate defense against viral infections (Haller et al. (1981) *J. Exp. Med.* 154:199; Lindenmann et al. (1981) *Methods Enzymol.* 78:181). More recent studies, however, implicate type I IFNs as potent immunoregulatory cytokines in the adaptive immune response. Specifically, type I IFNs have been shown to facilitate differentiation of naïve T cells along the Th1 pathway (Brinkmann et al. (1993) *J. Exp. Med.* 178:1655), to enhance antibody production (Finkelman et al. (1991) *J. Exp. Med.* 174:1179) and to support the functional activity and survival of memory T cells (Santini, et al. (2000) *J. Exp. Med.* 191:1777; Tough et al. (1996) *Science* 272:1947).

Recent work by a number of groups suggests that IFN-α may enhance the maturation or activation of dendritic cells (DCs) (Santini, et at (2000) *J. Exp. Med.* 191:1777; Luft et al. (1998) *J. Immunol.* 161:1947; Luft et al. (2002) *Int. Immunol.* 14:367; Radvanyi et al. (1999) *Scand. J. Immunol.* 50:499; Paquette et al. (1998) *J. Leukoc. Biol.* 64:358). Furthermore, increased expression of type I interferons has been described in numerous autoimmune diseases (Foulis et al. (1987) *Lancet* 2:1423; Hooks et al. (1982) *Arthritis Rheum* 25; 396; Hertzog et al. (1988) *Clin. Immunol. Immunopathol.* 48:192; Hopkins and Meager (1988) *Clin. Exp. Immunol.* 73:88; Arvin and Miller (1984) *Arthritis Rheum.* 27:582). The most studied examples of this are insulin-dependent diabetes mellitus (IDDM) (Foulis (1987) supra), systemic lupus erythematosus (SLE) (Hooks (1982) supra; Blanco et al. (2001) *Science* 294:1540; Ytterberg and Schnitzer (1982) *Arthritis Rheum.* 25:401; Batteux et al. (1999) *Eur. Cytokine Netw.:* 509), and autoimmune thyroiditis (Prummel and Laurberg (2003) *Thyroid* 13:547; Mazziotti et al. (2002) *J. Endocrinol. Invest.* 25:624; You et al. (1999) *Chin. Med. J.* 112:61; Koh et al. (1997) *Thyroid* 7:891), which are all associated with elevated levels of IFN α, and rheumatoid arthritis (RA) (Hertzog (1988), Hopkins and Meager (1988), Arvin and Miller (1984), supra) in which IFN-β may play a more significant role.

Moreover, administration of interferon α has been reported to exacerbate underlying disease in patients with psoriasis, autoimmune thyroiditis and multiple sclerosis and to induce an SLE like syndrome in patients without a previous history of autoimmune disease. Interferon α has also been shown to induce glomerulonephritis in normal mice and to accelerate the onset of the spontaneous autoimmune disease of NZB/W mice. Further, IFN-α therapy has been shown in some cases to lead to undesired side effects, including fever and neurological disorders. Hence, there are pathological situations in which inhibition of IFN-α activity may be beneficial to the patient and a need exists for agents effective in inhibiting IFN-α activity.

SUMMARY OF THE INVENTION

The present invention provides isolated monoclonal antibodies that bind to IFN alpha and inhibit the biological activity of multiple IFN alpha subtypes, but not substantially inhibit the biological activity of IFN alpha subtype 21, or of IFN beta or IFN omega. In preferred embodiments, the antibodies of the invention are capable of inhibiting surface expression of cell markers induced by IFN alpha, inhibiting IF-10 expression induced by IFN alpha and/or inhibiting dendritic cell development mediated by plasma from patients with systemic lupus erythematosus (SLE). These antibodies can be used for therapeutic, including prophylactic, purposes, for example in situations where the production or expression of interferon alpha is associated with pathological symptoms. Such antibodies can also be used for the diagnosis of various diseases or for the study of the evolution of such diseases.

In one embodiment, the present invention includes an antibody or antibody fragment that binds to IFN alpha, preferably human IFN alpha (e.g., human IFN alpha 2a, human IFN alpha 2b), and inhibits the biological activity of multiple IFN alpha subtypes, but does not substantially inhibit the biological activity of IFN alpha subtype 21, or IFN beta or IFN omega. In addition, in various embodiments, the antibodies of the invention are capable of inhibiting surface expression of cell markers induced by IFN alpha, inhibiting IP-10 expression induced by IFN alpha and/or inhibiting dendritic cell development mediated by plasma from patients with systemic lupus erythematosus (SLE). The antibody or antibody fragment preferably is a human antibody or antibody fragment, or alternatively can be a murine, chimeric or humanized antibody. In certain embodiments, an antibody of the invention functions by a non-competitive mechanism of action. For example, in preferred embodiments, the antibody: (i) does not inhibit the binding of an IFN alpha, such as IFN alpha 2a, to cells expressing interferon alpha receptor (IFNAR) and (ii) binds to cells expressing IFNAR in the presence of an IFN alpha, such as IFN alpha 2a.

In one aspect, the invention pertains to isolated antibodies, or antigen binding portions thereof, wherein the antibodies:
  (a) comprise a heavy chain variable region of a human VH 1-18 or 4-61 gene;
  (b) comprise a light chain variable region of a human A27 gene; and
  (c) inhibit the biological activity of interferon alpha (e.g., inhibits the biological activity of at least one IFN alpha subtype).

In another aspect, the invention pertains to isolated monoclonal antibodies, or antigen binding portions thereof, comprising a heavy chain variable region comprising CDR1, CDR2, and CDR3 sequences and a light chain variable region comprising CDR1, CDR2, and CDR3 sequences, wherein:
  (a) the heavy chain variable region CDR3 sequence comprises the amino acid sequence of SEQ ID NO: 7, 8, or 9, or conservative modifications thereof;
  (b) the light chain variable region CDR3 sequence comprises the amino acid sequence of SEQ ID NO: 16, 17, or 18, or conservative modifications thereof;
  (c) the antibody inhibits the biological activity of multiple IFN alpha subtypes but does not substantially inhibit the biological activity of IFN alpha 21; and
  (d) the antibody exhibits at least one of the following properties:
    (i) the antibody does not substantially inhibit the biological activity of IFN beta or IFN omega;
    (ii) the antibody inhibits IFN-induced surface expression of CD38 or MHC Class I on peripheral blood mononuclear cells;
    (iii) the antibody inhibits IFN-induced expression of IP-10 by peripheral blood mononuclear cells;
    (iv) the antibody inhibits dendritic cell development mediated by systemic lupus erythematosus (SLE) plasma.

In such antibodies, the heavy chain variable region CDR2 sequence can comprise the amino acid sequence of SEQ ID NO: 4, 5, or 6, or conservative modifications thereat and the light chain variable region CDR2 sequence can comprise the amino acid sequence of SEQ ID NO: 13, 14, or 15, or conservative modifications thereof. Furthermore, in such antibodies, the heavy chain variable region CDR1 sequence can comprise the amino acid sequence of SEQ ID NO: 1, 2, or 3, or conservative modifications thereof; and the light chain variable region CDR1 sequence can comprise the amino acid sequence of SEQ ID NO: 10, 11, or 12, or conservative modifications thereof.

In another aspect, the invention pertains to isolated monoclonal antibodies, or antigen binding portions thereof, comprising a heavy chain variable region and a light chain variable region, wherein:
  (a) the heavy chain variable region comprises an amino acid sequence that is at least 80% homologous to SEQ ID NO: 19, 20, or 21;
  (b) the light chain variable region comprises an amino acid sequence that is at least 80% homologous to SEQ ID NO: 22, 23, or 24;
  (c) the antibody inhibits the biological activity of multiple IFN alpha subtypes but does not substantially inhibit the biological activity of IFN alpha 21; and
  (d) the antibody exhibits at least one of the following properties:
    (i) the antibody does not substantially inhibit the biological activity of IFN beta or IFN omega;
    (ii) the antibody inhibits IFN-induced surface expression of CD38 or MI-IC Class I on peripheral blood mononuclear cells;
    (iii) the antibody inhibits IFN-induced expression of IP-10 by peripheral blood mononuclear cells;
    (iv) the antibody inhibits dendritic cell development mediated by systemic lupus erythematosus (SLE) plasma.

In another aspect, the invention pertains to isolated monoclonal antibodies, or antigen binding portions thereof, comprising a heavy chain variable region and a light chain variable region, wherein:
  (a) the heavy chain variable region comprises an amino acid sequence comprising the amino acid sequence of SEQ ID NO: 19, 20, or 21; and
  (b) the light chain variable region comprises an amino acid comprising the amino acid sequence of SEQ ID NO: 22, 23, or 24;
wherein the antibody inhibits the biological activity of interferon alpha (e.g., inhibits the biological activity of at least one IFN alpha subtype).

In yet another aspect, the invention pertains to mutated variants of SEQ ID NO: 19 having increased stability. Preferred embodiments include an isolated monoclonal antibody, or antigen binding portion thereof comprising:
  (a) a heavy chain variable region comprising an amino acid sequence selected from the group consisting of SEQ ID NOs: 34, 35, 36 and 37; and
  (b) a light chain variable region comprising the amino acid sequence of SEQ ID NO: 22;
wherein the antibody inhibits the biological activity of at least one interferon alpha subtype.

In yet another aspect, the invention pertains to an isolated monoclonal antibody, or antigen binding portion thereof comprising:
  (a) a heavy chain variable region CDR1 comprising an amino acid sequence selected from the group consisting of SEQ ID NOs: 1, 2 and 3;
  (b) a heavy chain variable region CDR2 comprising an amino acid sequence selected from the group consisting of SEQ ID NOs: 4, 5 and 6;
  (c) a heavy chain variable region CDR3 comprising an amino acid sequence selected from the group consisting of SEQ ID NOs: 7, 8 and 9;
  (d) a light chain variable region CDR1 comprising an amino acid sequence selected from the group consisting of SEQ ID NOs: 10, 11 and 12;
  (e) a light chain variable region CDR2 comprising an amino acid sequence selected from the group consisting of SEQ ID NOs: 13, 14 and 15; and
  (f) a light chain variable region CDR3 comprising an amino acid sequence selected from the group consisting of SEQ ID NOs: 16, 17 and 18;

wherein the antibody inhibits the biological activity of interferon alpha (e.g., inhibits the biological activity of at least one IFN alpha subtype).

In yet another aspect, the invention pertains to an isolated monoclonal antibody, or antigen binding portion thereof, that competes for binding to IFN alpha 2a or IFN alpha 2b with any of the above mentioned antibodies.

In yet another aspect, the invention pertains to an isolated human antibody, or antigen-binding portion thereof, that inhibits the biological activity of multiple interferon (IFN) alpha subtypes, wherein the antibody does not inhibit binding of IFN alpha to interferon alpha receptor (IFNAR)-expressing cells and wherein the antibody associates with IFNAR-expressing cells in the presence, but not the absence, of IFN alpha.

The invention also encompasses nucleic acid molecules that encode the antibodies or antigen-binding portions thereof in any of the above mentioned antibodies.

The antibodies of the invention can be of any isotype. Preferred antibodies are of the IgG1 or IgG4 isotype. The antibodies of the invention can be full-length antibodies comprising variable and constant regions, or they can be antigen-binding fragments thereof, such as a single chain antibody or a Fab fragment.

The invention also encompasses immunoconjugates of the antibodies of the invention, in which the antibody is linked to a therapeutic agent, such as a cytotoxin or a radioactive isotope. The invention also encompasses bispecific molecules comprising an antibody of the invention, in which the antibody is linked to a second functional moiety having a different binding specificity than the antibody.

Pharmaceutical compositions comprising an antibody, or antigen binding portion thereof, or immunoconjugate or bispecific molecule thereof, are also provided. Such pharmaceutical compositions comprise the active agent and a pharmaceutically acceptable carrier.

In another aspect, the present invention includes a method of inhibiting the biological activity of interferon alpha, either in vivo or in vitro, comprising contacting interferon alpha with an anti-IFN alpha antibody of the invention, such that the biological activity of interferon alpha is inhibited.

In another aspect, the present invention includes a method of treating an interferon alpha-mediated disease or disorder in a subject, comprising administering to the subject an anti-IFN alpha antibody of the invention, such that the interferon-alpha mediated disease in the subject is treated. Examples of diseases that can be treated include autoimmune diseases (e.g., systemic lupus erythematosus, multiple sclerosis, insulin dependent diabetes mellitus, inflammatory bowel disease, psoriasis, autoimmune thyroiditis, rheumatoid arthritis and glomerulonephritis), transplant rejection and graft versus host disease.

Other features and advantages of the instant invention will be apparent from the following detailed description and examples, which should not be construed as limiting. The contents of all references, patents and published patent applications cited throughout this application are expressly incorporated herein by reference.

BRIEF DESCRIPTION OF THE DRAWINGS

FIG. 1A shows the nucleotide sequence (SEQ ID NO: 25) and amino acid sequence (SEQ ID NO: 19) of the heavy chain variable region of the 13H5 human monoclonal antibody. The CDR1 (SEQ ID NO: 1), CDR2 (SEQ II) NO: 4) and CDR3 (SEQ ID NO: 7) regions are delineated and the V, D and J germline derivations are indicated.

FIG. 1B shows the nucleotide sequence (SEQ ID NO: 28) and amino acid sequence (SEQ ID NO: 22) of the light chain variable region of the 13H5 human monoclonal antibody. The CDR1 (SEQ ID NO: 10), CDR2 (SEQ ID NO: 13) and CDR3 (SEQ ID NO: 16) regions are delineated and the V and J germline derivations are indicated.

FIG. 2A shows the nucleotide sequence (SEQ ID NO: 26) and amino acid sequence (SEQ ID NO: 20) of the heavy chain variable region of the 13H7 human monoclonal antibody. The CDR1 (SEQ ID NO: 2), CDR2 (SEQ ID NO: 5) and CDR3 (SEQ ID NO: 8) regions are delineated and the V, D and J germline derivations are indicated.

FIG. 2B shows the nucleotide sequence (SEQ ID NO: 29) and amino acid sequence (SEQ ID NO: 23) of the light chain variable region of the 13H7 human monoclonal antibody. The CDR1 (SEQ ID NO: 11), CDR2 (SEQ ID NO: 14) and CDR3 (SEQ ID NO: 17) regions are delineated and the V and J germline derivations are indicated.

FIG. 3A shows the nucleotide sequence (SEQ ID NO: 27) and amino acid sequence (SEQ ID NO: 21) of the heavy chain variable region of the 7H9 human monoclonal antibody. The CDR1 (SEQ ID NO: 3), CDR2 (SEQ ID NO: 6) and CDR3 (SEQ ID NO: 9) regions are delineated and the V, D and J germline derivations are indicated.

FIG. 3B shows the nucleotide sequence (SEQ ID NO: 30) and amino acid sequence (SEQ ID NO: 24) of the light chain variable region of the 7H9 human monoclonal antibody. The CDR1 (SEQ ID NO: 12), CDR2 (SEQ ID NO: 15) and CDR3 (SEQ ID NO: 18) regions are delineated and the V and J germline derivations are indicated.

FIG. 4 shows the alignment of the amino acid sequence of the heavy chain variable region of 13H5 (SEQ ID NO:19) and 7H9 (SEQ ID NO:21) with the human germline VH 1-18 amino acid sequence (SEQ ID NO: 31).

FIG. 5 shows the alignment of the amino acid sequence of the heavy chain variable region of 131-17 (SEQ ID NO:20) with the human germline VH 4-61 amino acid sequence (SEQ ID NO: 32).

FIG. 6 shows the alignment of the amino acid sequence of the light chain variable region of 13H5 (SEQ ID NO:22), 13H7 (SEQ ID NO:23) and 7H9 (SEQ ID NO:24) with the human germline VK A27 amino acid sequence (SEQ ID NO: 33).

DETAILED DESCRIPTION OF THE INVENTION

Figure 7:
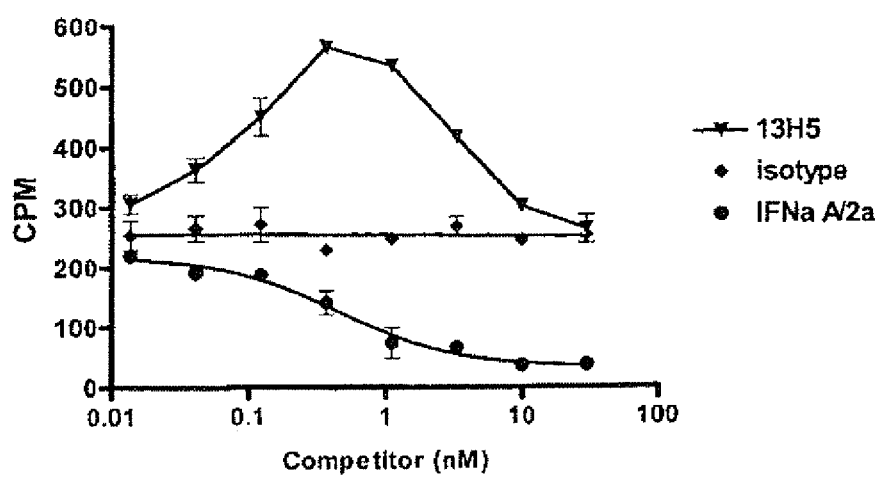
FIG. 7 is a graph showing competition of binding of $^{125}$I-IFNα 2a to IFNAR-expressing Daudi cells by unlabeled IFNα 2a (•) versus enhancement of $^{125}$I-IFNα 2a binding by mAb 13H5 (▼). An isotype control antibody had no effect on binding (♦).

The present invention relates to isolated monoclonal antibodies that bind to IFN alpha and that are capable of inhibiting the biological activity of multiple IFN alpha subtypes, but not the biological activity of IFN alpha subtype 21, or IFN beta or IFN omega. The antibodies of the invention are capable of inhibiting surface expression of cell markers induced by IFN alpha, inhibiting IP-10 expression induced by IFN alpha and inhibiting dendritic cell development mediated by plasma from patients with systemic lupus erythematosus (SLE). The invention provides isolated antibodies, methods of making such antibodies, immunoconjugates and bispecific molecules comprising such antibodies and pharmaceutical compositions containing the antibodies, immunoconjugates or bispecific molecules of the invention. The invention also relates to methods of using the antibodies to inhibit IFN alpha activity, for example in the treatment of autoimmune disorders, or for inhibiting or preventing transplant rejection or in the treatment of graft versus host disease.

In order that the present invention may be more readily understood, certain terms are first defined. Additional definitions are set forth throughout the detailed description.

The terms "interferon alpha" and "IFN alpha" are used interchangeably and intended to refer to IFN alpha proteins encoded by a functional gene of the interferon alpha gene locus with 75% or greater sequence identity to IFN alpha 1 (Genbank number NP 076918 or protein encoded by Genbank number NM 024013). Examples of IFN alpha subtypes include IFN alpha 1, alpha 2a, alpha 2b, alpha 4, alpha 5, alpha 6, alpha 7, alpha 8, alpha 10, alpha 13, alpha 14, alpha 16, alpha 17 and alpha 21. The term "interferon alpha" is intended to encompass recombinant forms of the various IFN alpha subtypes, as well as naturally occurring preparations that comprise IFN alpha proteins, such as leukocyte IFN and lymphoblastoid IFN. The term IFN alpha is not intended to encompass IFN omega alone, although a composition that comprises both IFN alpha and IFN omega is encompassed by the term IFN alpha.

The term "IFN alpha receptor" as used herein is intended to refer to members of the IFN alpha receptor family of molecules that are receptors for the ligand IFN alpha. Examples of IFN alpha receptors are IFN alpha receptor I and IFN alpha receptor 2.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present invention is the IFN alpha receptor I or IFN alpha receptor 2.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., IFN alpha). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$, and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward at al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird at al. (1988) *Science* 242:423-426; and Huston at al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds IFN alpha is substantially free of antibodies that specifically bind antigens other than IFN alpha). An isolated antibody that specifically binds IFN alpha may, however, have cross-reactivity to other antigens, such as IFN alpha molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

As used herein, an antibody that "inhibits the biological activity" of an IFN alpha subtype is intended to refer to an antibody that inhibits the activity of that subtype by at least 10%, more preferably at least 20%, 30%, 40%, 50%, 60%, 70% or 80%, as compared to the level of activity in the absence of the antibody, for example using a functional assay such as those described in the Examples, such as the Daudi cell proliferation assay. Alternatively, an antibody that "inhibits the biological activity" of an IFN alpha subtype can refer to an antibody that inhibits the activity of that subtype with an $EC_{50}$ of less than 200 nM or less, more preferably 100 nM or less, even more preferably 50 nM or less and even more preferably 10 nM or less.

As used herein, an antibody that "does not substantially inhibit the biological activity" of an IFN alpha subtype, or of IFN beta or IFN omega, is intended to refer to an antibody that inhibits the activity of that subtype by at less than 10%, more preferably by less than 5% and even more preferably by essentially undetectable amounts. Alternatively, an antibody that "does not inhibit the biological activity" of an IFN alpha subtype can refer to an antibody that inhibits the activity of that subtype with an $EC_{50}$ of 300 nM or greater.

As used herein, "specific binding" refers to antibody binding to a predetermined antigen. Typically, the antibody binds with a dissociation constant ($K_D$) of $10^{-8}$ M or less, and binds to the predetermined antigen with a $K_D$ that is at least two-fold less than its $K_D$ for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

The term "$K_{assoc}$" or "$K_a$", as used herein, is intended to refer to the association rate of a particular antibody-antigen interaction, whereas the term "$K_{dis}$" or "$K_d$" as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $10^{-8}$ M or less, more preferably $10^{-9}$ M or less and even more preferably $10^{-10}$ M or less. However, "high affinity" binding can vary for other antibody isotypes. For example, "high affinity" binding for an IgM isotype refers to an antibody having a KD of $10^{-7}$ M or less, more preferably $10^{-8}$ M or less.

As used herein, the term "subject" includes any human or nonhuman animal. The term "nonhuman animal" includes all vertebrates, e.g., mammals and non-mammals, such as non-human primates, sheep, dogs, cats, horses, cows chickens, amphibians, reptiles, etc.

Various aspects of the invention are described in further detail in the following subsections.

Anti-IFN Alpha Antibodies

The antibodies of the invention are characterized by particular functional features or properties of the antibodies. For example, in particular embodiments, the antibodies bind specifically to multiple subtypes of IFN alpha, such as IFN alpha 2a and IFN alpha 2b. Preferably, an antibody of the invention binds to IFN alpha 2a and/or alpha 2b with high affinity, for example with a $K_D$ of $10^{-8}$ M or less or $10^{-9}$ M or less or even $10^{-10}$ M or less. In a preferred embodiment, the antibody binds to human IFN alpha 2a and human IFN alpha 2b. The binding affinity and kinetics of the antibodies of the invention can be examined by, for example, Biacore analysis as described in the Examples.

Furthermore, in other embodiments, the antibodies of the invention exhibit various functional properties. For example, the antibodies may be capable of inhibiting the biological activity of multiple IFN alpha subtypes but may not substantially inhibit the biological activity of IFN alpha 21. The antibodies also may not substantially inhibit the biological activity of IFN beta or IFN omega. The antibodies of the invention also may be capable of inhibiting IFN-induced surface expression of cell markers, such as CD38 or MHC Class I, on normal human peripheral blood mononuclear cells. The antibodies also may be capable of inhibiting IFN-induced expression of IP-10 by normal human peripheral blood mononuclear cells. Inhibition of biological activity of MN alpha subtypes, IFN beta and/or TEN omega can be evaluated using functional assays such as those described in the Examples, such as a Daudi cell proliferation assay.

Still further, the antibodies may be capable of inhibiting dendritic cell development mediated by plasma of patients with systemic lupus erythematosus (SLE). Dendritic cell development can be assessed by examining the expression of cell surface markers, such as CD38, MHC Class I and/or CD123, as described in the Examples.

In certain preferred embodiments, an antibody of the invention inhibits the biological activity of IFN alpha by a non-competitive mechanism of action, i.e., the antibody does not compete for binding of IFN alpha to IFNAR. Rather, such an antibody becomes associated with cell-surface IFNAR in the presence of IFN alpha and inhibits cell signaling through IFNAR. In other preferred embodiments, an antibody having these binding properties does not exhibit significant ADCC activity. Assays for examining these functional properties of the antibody are known in the art, such as the assays described in Examples 8 and 9. For example, the ability of the antibody to inhibit binding of radiolabeled IFN alpha to IFNAR-expressing cells can be examined. The inability of the antibody to inhibit the binding of radiolabeled IFN alpha to IFNAR is indicative of a non-competitive mechanism of action. To further examine this mechanism of action, the binding of radiolabeled antibody, in the presence or absence of IFN alpha, to IFNAR-expressing cells can be assayed. Binding of the radiolabeled antibody to IFNAR-expressing cells in the presence, but not the absence, of IFN alpha is indicative this mechanism of action.

In a preferred embodiment, antibodies of the invention bind to the IFN alpha-IFNAR complex with a greater affinity (e.g., $K_D$) than to IFN alpha alone (one or more subtypes) and/or to IFNAR alone. For example, in certain embodiments, antibodies of the invention bind the IFN alpha-IFNAR complex with a $K_D$ of $10^{-8}$ M or greater affinity, a $K_D$ of $10^{-9}$ M or greater affinity, or a $K_D$ of $10^{-10}$ M or greater affinity.

In another preferred embodiment, antibodies of the invention are bispecific for IFN alpha (one or more subtypes) and IFNAR (IFNAR1 and/or IFNAR2), meaning that the antibodies associate with both IFN alpha and IFNAR (IFNAR1 and/or IFNAR2). Accordingly, the present invention includes bispecific molecules comprising at least one first binding specificity for IFN alpha and a second binding specificity for IFNAR1, wherein, for example, the second binding specificity for IFNAR1 can be formed by the association of the antibody with IFN alpha. The present invention also includes bispecific molecules comprising at least one binding specificity for IFN alpha and a second binding specificity for IFNAR2, wherein, for example, the second binding specificity for INFAR2 can be formed by association of the antibody with IFN alpha.

Monoclonal Antibodies 13H5, 13H7 and 7H9

Preferred antibodies of the invention are the human monoclonal antibodies 13H5, 13H7, and 7H9, isolated and structurally characterized as described in the Examples. The $V_H$ amino acid sequences of 13H5, 13H7, and 7H9 are shown in SEQ ID NOs: 19, 20, and 21, respectively. The $V_L$ amino acid sequences of 13H5, 13H7, and 7H9 are shown in SEQ ID NOs: 22, 23 and 24, respectively. Given that each of these antibodies can bind to IFN alpha, the $V_H$ and $V_L$ sequences can be "mixed and matched" to create other anti-IFN alpha binding molecules of the invention. IFN alpha binding or neutralizing activity of such "mixed and matched" antibodies can be tested using the binding assays described above and in the Examples (e.g., ELISA, Biacore analysis, Daudi cell proliferation assay). Preferably, the $V_H$ sequences of 13H5 and 7H9 are mixed and matched, since these antibodies use $V_H$ sequences derived from the same germline sequence (VH 1-18) and thus they exhibit structural similarity. Additionally or alternatively, the $V_L$ sequences of 13H5, 13H7 and 7H9 can be mixed and matched, since these antibodies use $V_1$ sequences derived from the same germline sequence ($V_k$ A27) and thus they exhibit structural similarity.

Accordingly, in one aspect, the invention provides an isolated monoclonal antibody, or antigen binding portion thereof, comprising:

(a) a heavy chain variable region comprising an amino acid sequence selected from the group consisting of SEQ ID NOs: 19, 20, and 21; and (b) a light chain variable region comprising an amino acid sequence selected from the group consisting of SEQ ID NOs: 22, 23, and 24;

wherein the antibody inhibits the biological activity of interferon alpha.

Preferred heavy and light chain combinations include:

(a) a heavy chain variable region comprising the amino acid sequence of SEQ ID NO: 19; and (b) a light chain variable region comprising the amino acid sequence of SEQ ID NO:22; or (a) a heavy chain variable region comprising the amino acid sequence of SEQ ID NO: 20; and (b) a light chain variable region comprising the amino acid sequence of SEQ ID NO:23; or (a) a heavy chain variable region comprising the amino acid sequence of SEQ ID NO: 21; and (b) a light chain variable region comprising the amino acid sequence of SEQ ID NO:24.

In another aspect, the invention provides antibodies that comprise the heavy chain and light chain CDR1s, CDR2s, and CDR3s of 13H5, 13H7, and 7H9, or combinations thereof. The amino acid sequences of the $V_H$ CDR1s of 13H5, 13H7, and 7H9 are shown in SEQ 1N NOs: 1, 2, and 3. The amino acid sequences of the $V_H$ CDR2s of 13H5, 13H7, and 7H9 are shown in SEQ 1N NOs: 4, 5, and 6. The amino acid sequences of the $V_H$ CDR3s of 13H5, 13H7, and 7H9 are shown in SEQ 1N NOs: 7, 8, and 9. The amino acid sequences of the $V_L$ CDR1s of 13H5, 13H7, and 7H9 are shown in SEQ 1N NOs: 10, 11, and 12. The amino acid sequences of the $V_L$ CDR2s of 13H5, 13H7, and 7H9 are shown in SEQ 1N NOs: 13, 14, and 15. The amino acid sequences of the $V_L$ CDR3s of 13H5, 13H7, and 7H9 are shown in SEQ 1N NOs: 16, 17, and 18. The CDR regions are delineated using the Kabat system (Kabat. E. A., et al. (1991) Sequences of Proteins of Immunological Interest, Fifth Edition, U.S. Department of Health and Human Services, NIH Pulibcation No. 91-3242).

Given that each of these antibodies was selected based on IFN binding activity and that antigen-binding specificity is provided primarily by the CDR1, 2 and 3 regions, the $V_H$ CDR1, 2 and 3 sequences and $V_L$ CDR1, 2 and 3 sequences can be "mixed and matched" (i.e., CDRs from different antibodies can be mixed and match, although each antibody must contain a $V_H$ CDR1, 2 and 3 and a $V_L$ CDR1, 2 and 3) to create other anti-IFN alpha molecules of the invention. IFN alpha binding of such "mixed and matched" antibodies can be tested using the binding assays described in the Examples (e.g., ELISA and/or Biacore). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence preferably is replaced with a structurally similar CDR sequence(s). For example, the $V_H$ CDR1s of 13H5 and 7119 share some structural similarity and therefore are amenable to mixing and matching. It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies antibodies 13H5, 13H7 and 7H9.

Accordingly, in another aspect, the invention provides an isolated monoclonal antibody, or antigen binding portion thereof comprising:

(a) a heavy chain variable region CDR1 comprising an amino acid sequence selected from the group consisting of SEQ ID NOs: 1, 2, and 3;

(b) a heavy chain variable region CDR2 comprising an amino acid sequence selected from the group consisting of SEQ ID NOs: 4, 5, and 6;

(c) a heavy chain variable region CDR3 comprising an amino acid sequence selected from the group consisting of SEQ ID NOs: 7, 8, and 9;

(d) a light chain variable region CDR1 comprising an amino acid sequence selected from the group consisting of SEQ ID NOs: 10, 11, and 12;

(e) a light chain variable region CDR2 comprising an amino acid sequence selected from the group consisting of SEQ ID NOs: 13, 14, and 15; and (f) a light chain variable region CDR3 comprising an amino acid sequence selected from the group consisting of SEQ ID NOs: 16, 17, and 18;

wherein the antibody the antibody inhibits the biological activity of interferon alpha.

In a preferred embodiment, the antibody comprises:

(a) a heavy chain variable region CDR1 comprising SEQ ID NO: 1;

(b) a heavy chain variable region CDR2 comprising SEQ ID NO: 4;

(c) a heavy chain variable region CDR3 comprising SEQ ID NO: 7;

(d) a light chain variable region CDR1 comprising SEQ ID NO: 10;

(e) a light chain variable region CDR2 comprising SEQ ID NO: 13; and (t) a light chain variable region CDR3 comprising SEQ ID NO: 16.

In another preferred embodiment, the antibody comprises:

(a) a heavy chain variable region CDR1 comprising SEQ ID NO: 2;

(b) a heavy chain variable region CDR2 comprising SEQ ID NO: 5;

(c) a heavy chain variable region CDR3 comprising SEQ ID NO: 8;

(d) a light chain variable region CDR1 comprising SEQ ID NO: 11;

(e) a light chain variable region CDR2 comprising SEQ ID NO: 14; and (1) a light chain variable region CDR3 comprising SEQ ID NO: 17.

In another preferred embodiment, the antibody comprises:

(a) a heavy chain variable region CDR1 comprising SEQ ID NO: 3;

(b) a heavy chain variable region CDR2 comprising SEQ ID NO: 6;

(c) a heavy chain variable region CDR3 comprising SEQ ID NO: 9;

(d) a light chain variable region CDR1 comprising SEQ ID NO: 12;

(e) a light chain variable region CDR2 comprising SEQ ID NO: 15; and (f) a light chain variable region CDR3 comprising SEQ ID NO: 18.

Antibodies Having Particular Germline Sequences

In certain embodiments, an antibody of the invention comprises a heavy chain variable region from a particular germline heavy chain immunoglobulin gene and/or a light chain variable region from a particular germline Tight chain immunoglobulin gene.

For example, in a preferred embodiment, the invention provides an isolated monoclonal antibody, or an antigen-binding portion thereof, therein the antibody:

(a) comprises a heavy chain variable region of a human VH 1-18 or 4-61 gene;

(b) comprises a light chain variable region of a human Vk A27 gene; and (c) the antibody inhibits the biological activity of interferon alpha.

In one embodiment, the antibody comprises a heavy chain variable region of a human VH 1-18 gene. Examples of antibodies having a VH and Vk gene sequence of VH 1-18 and Vk A27, respectively, include 13H5 and 7H9. In another embodiment, the antibody comprises a heavy chain variable region of a human VH 4-61 gene. An example of an antibody having a VH and Vk gene sequence of VH 4-61 and Vk A27, respectively, is 13H7.

As used herein, a human antibody comprises heavy or light chain variable regions "of" the products of) or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest A human antibody that is "of" (i.e., the product of) or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "of" (i.e., the product of) or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-IFN alpha antibodies of the invention.

For example, the invention provides an isolated monoclonal antibody, or antigen binding portion thereof, comprising a heavy chain variable region and a light chain variable region, wherein:

(a) the heavy chain variable region comprises an amino acid sequence that is at least 80% homologous to an amino acid sequence selected from the group consisting of SEQ ID NOs: 19, 20, and 21;

(b) the light chain variable region comprises an amino acid sequence that is at least 80% homologous to an amino acid sequence selected from the group consisting of SEQ ID NOs: 22, 23, and 24;

(c) the antibody inhibits the biological activity of multiple IFN alpha subtypes but does not substantially inhibit the biological activity of IFN alpha 21;

(d) the antibody exhibits at least one of the following properties:
  (i) the antibody does not substantially inhibit the biological activity of IFN beta or IFN omega;
  (ii) the antibody inhibits IFN-induced surface expression of CD38 or MHC Class I on peripheral blood mononuclear cells;
  (iii) the antibody inhibits IFN-induced expression of IP-10 by peripheral blood mononuclear cells;
  (iv) the antibody inhibits dendritic cell development mediated by systemic lupus erythematosus (SLE) plasma.

In other embodiments, the $V_H$ and/or $V_L$ amino acid sequences may be 85%, 90%, 95%©, 96%, 97%, 98% or 99% homologous to the sequences set forth above. An antibody having $V_H$ and $V_L$ regions having high (i.e., 80% or greater) homology to the $V_H$ and $V_L$ regions of SEQ ID NOs; 19, 20, and 21 and 22, 23, and 24, respectively, can be obtained by mutagenesis (e.g., site-directed or PCR-mediated mutagenesis) of nucleic acid molecules encoding SEQ ID NOs: 19, 20, and 21 and/or 22, 23, and 24, followed by testing of the encoded altered antibody for retained function (i.e., the functions set forth in (c) and (d) above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 13H5, 13117, or 7H9), or conservative modifications thereof, and wherein the antibodies retain the desired functional properties of the anti-IFN alpha antibodies of the invention. For example, preferred antibodies of the invention include those in which the heavy chain variable region CDR3 sequence comprises the amino acid sequence of SEQ ID NO: 3, or conservative modifications thereof; and the light chain variable region CDR3 sequence comprises the amino acid sequence of SEQ ID NO: 6, or conservative modifications thereof. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises the amino acid sequence selected from the group consisting of SEQ ID NO: 7, 8, and 9, and conservative modifications thereof;

(b) the light chain variable region CDR3 sequence comprises the amino acid sequence selected from the group consisting of SEQ ID NO: 16, 17, and 18, and conservative modifications thereof;

(c) the antibody inhibits the biological activity of multiple IFN alpha subtypes but does not substantially inhibit the biological activity of IFN alpha 21;

(d) the antibody exhibits at least one of the following properties:
  (i) the antibody does not substantially inhibit the biological activity of IFN beta or IFN omega;
  (ii) the antibody inhibits IFN-induced surface expression of CD38 or MHC Class I on peripheral blood mononuclear cells;
  (iii) the antibody inhibits IFN-induced expression of IP-10 by peripheral blood mononuclear cells;
  (iv) the antibody inhibits dendritic cell development mediated by systemic lupus erythematosus (SLE) plasma.

In a further embodiment, the heavy chain variable region CDR2 sequence comprises the amino acid sequence selected from the group consisting of amino acid sequences of SEQ ID NO: 4, 5, and 6, and conservative modifications thereof; and the light chain variable region CDR2 sequence comprises the amino acid sequence selected from the group consisting of amino acid sequences SEQ ID NO: 13, 14, and 15, and conservative modifications thereof. In a still further embodiment, the heavy chain variable region CDR1 sequence comprises the amino acid sequence selected from the group consisting of amino acid sequences of SEQ ID NO: 1,2, and 3, and conservative modifications thereof; and the light chain variable region CDR1 sequence comprises the amino acid sequence selected from the group consisting of amino acid sequences of SEQ ID NO: 10, 11, and 12, and conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c) and (d) above) using the functional assays described herein.

Antibodies that Bind to the Same Epitope as Anti-IFN Alpha Antibodies of the Invention In another embodiment, the invention provides antibodies that bind to the same epitope as do the various human IFN alpha antibodies of the invention provided herein, such as other human antibodies that bind to the same epitope as the 13H5, 13H7, and 7H9 antibodies described herein. Such antibodies can be identified based on their ability to cross-compete (e.g., to competitively inhibit the binding of in a statistically significant manner) with other antibodies of the invention, such as 13H5, 13H7 or 7H9, in standard IFN alpha binding assays. For example, as demonstrated in the Examples by Biacore analysis, 13H5 binds with high affinity to IFN alpha 2a and IFN alpha 2b. Accordingly, in one embodiment, the invention provides antibodies, preferably human antibodies, that compete for binding to IFN alpha 2a or IFN alpha 2b with another antibody of the invention (e.g., 13H5, 13H7 or 7H9). The ability of a test antibody to inhibit the binding of, e.g., 13H5, 13H7 or 7H9 to IFN alpha 2a or IFN alpha 2b demonstrates that the test antibody can compete with that antibody for binding toIFN alpha 2a or IFN alpha 2b; such an antibody may, according to non-limiting theory, bind to the same or a related (e.g., a structurally similar or spatially proximal) epitope on IFN alpha 2a or IFN alpha 2b as the antibody with which it competes. In a preferred embodiment, the antibody that binds to the same epitope on IFN alpha 2a or IFN alpha 2b as, e.g., 13H5, 13H7, or 71-19, is a human monoclonal antibody. Such human monoclonal antibodies can be prepared and isolated as described in the Examples.

Engineered and Modified Antibodies

An antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_1$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L, et al. (1998) *Nature* 332:323-327; Jones, P. et al. (1986) *Nature* 321:522-525; Queen, C. et al. (1989) *Proc. Natl. Acad. Sci. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated monoclonal antibody, or antigen binding portion thereof, comprising a heavy chain variable region comprising CDR1, CDR2, and CDR3 sequences comprising the amino acid sequences selected from the group consisting of SEQ ID NO: 1, 2, and 3, SEQ ID NO: 4, 5, and 6 and SEQ ID NO: 7, 8, and 9, respectively, and a light chain variable region comprising CDR1, CDR2, and CDR3 sequences comprising the amino acid sequences selected from the group consisting of SEQ ID NO:10, 11, and 12, SEQ ID NO: 13, 14, and 15 and SEQ ID NO: 16, 17, and 18, respectively. Thus, such antibodies contain the $V_H$ and $V_1$ CDR sequences of monoclonal antibodies 13H5, 13H7 or 7H9, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NTH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

Preferred framework sequences for use in the antibodies of the invention are those that are structurally similar to the framework sequences used by selected antibodies of the invention, e.g., similar to the VH 1-18 or 4-61 and VK A27 framework sequences used by the preferred monoclonal antibodies of the invention. The $V_H$ CDR1, 2 and 3 sequences, and the $V_L$ CDR1, 2 and 3 sequences can be grafted onto framework regions that have the same sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest, Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues are altered within a CDR region are altered.

Accordingly, in another embodiment, the invention provides isolated anti-IFN alpha monoclonal antibodies, or antigen binding portions thereof, comprising a heavy chain variable region comprising: (a) a $V_H$ CDR1 region comprising an amino acid sequence selected from the group consisting of SEQ ID NOs: 1, 2, and 3, or an amino acid sequence having one, two, three, four or five amino acid substitutions, deletions or additions as compared to SEQ ID NOs: 1, 2, or 3; (b) a $V_H$ CDR2 region comprising an amino acid sequence selected from the group consisting of SEQ ID NOs; 4, 5, and 6, or an amino acid sequence having one, two, three, four or five amino acid substitutions, deletions or additions as compared to SEQ ID NOs: 4, 5, or 6; (c) a $V_H$ CDR3 region comprising an amino acid sequence selected from the group consisting of SEQ ID NOs: 7, 8, and 9, or an amino acid sequence having one, two, three, four or five amino acid substitutions, deletions or additions as compared to SEQ ID NOs: 7, 8, or 9; (d) a $V_L$ CDR1 region comprising an amino acid sequence selected from the group consisting of SEQ ID NOs: 10, 11, and 12, or an amino acid sequence having one, two, three, four or five amino acid substitutions, deletions or additions as compared to SEQ ID NOs: 10, 11, or 12; (e) a $V_L$ CDR2 region comprising an amino acid sequence selected from the group consisting of SEQ ID NOs: 13, 14, and 15, or an amino acid sequence having one, two, three, four or five amino acid substitutions, deletions or additions as compared to SEQ ID NOs: 13, 14, or 15; and (1) a $V_L$ CDR3 region comprising an amino acid sequence selected from the group consisting of SEQ ID NOs: 16, 17, and 18, or an amino acid sequence having one, two, three, four or five amino acid substitutions, deletions or additions as compared to SEQ ID NOs: 16, 17, or 18.

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. For example, for 13H5, amino acid residue #81 (within FR3) of $V_H$ is a leucine whereas this residue in the corresponding VH 1-18 germline sequence is a methionine (see FIG. 4). To return the framework region sequences to their germline configuration, the somatic mutations can be "backmutated" to the germline sequence by, for example, site-directed mutagenesis or PCR-mediated mutagenesis (e.g., residue 81 of the $V_H$ of 13H5 can be "backmutated" from leucine to methionine). Such "backmutated" antibodies are also intended to be encompassed by the invention.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter it's glycosylation, again to alter one or more functional properties of the antibody. Each of these embodiments is described in further detail below. The numbering of residues in the Fe region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fe-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the Cl component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγRI, FcγRII, FcγRIII and FcRn have been described and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180).

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivative other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Modified Antibodies with Increased Stability

In another aspect, the invention provides modified forms of the 13H5 antibody that exhibit increased stability as compared to wild-type 13H5. As described in further detail in Example 10, the 13H5 antibody contains a deamidation site at Asn-55 within CDR2 of the $V_H$ chain. The amino acid sequence at this site, from positions 55 to 58) is N G N T (amino acid residues 55-58 of SEQ ID NO: 19). Accordingly, in certain embodiments, the amino acid sequence of the 13H5 $V_H$ chain is mutated at position 55 from asparagine to a different amino acid. Additionally or alternatively, amino acid positions around Asn-55 that influence deamidation can be mutated. Preferred amino acid substitutions at position 55 include aspartic acid and glutamine, with glutamine being more preferred. The amino acid sequence of 13H5 with a N55D substitution is shown in SEQ ID NO: 34. The amino acid sequence of 13H5 with a N55Q substitution is shown in SEQ ID NO: 35. In another embodiment, Asn-57 of the 13H5 $V_H$ chain is also mutated, together with mutation of Asn-55. A preferred amino acid substitution at position 57 is glutamine. The amino acid sequence of 13H5 with N55Q and N57Q substitutions is shown in SEQ ID NO: 36. These three mutated antibodies exhibit increased stability, under forced deamidation conditions, as compared to wild-type 13H5, as described further in Example 11.

In another embodiment, the glycine at amino acid position 56 is mutated to an alanine (G56A), since it has been determined from model peptides that the rate of deamidation is approximately 20-fold less with an alanine adjacent to the asparagine, rather than a glycine adjacent to the alanine (see e.g., Ahern, T. and Manning, M. C., eds. *Stability of Protein Pharmaceuticals*, Pharmaceutical Biotechnology, volume 2, chapter 1, pages 1-30). Thus, the G56A mutation represents a balance between decreased reactivity and minimal structural change to the wild type sequence, thus increasing stability while maintaining activity. The amino acid sequence of 13H5 with a 056A substitution is shown in SEQ ID NO; 37.

Accordingly, in various embodiments, the invention provides an IFN alpha antibody of the invention having an amino acid substitution at Asn-55, Gly-56 and/or Asn-57 of the CDR2 of the 13H5 $V_H$ chain, the wild type sequence of which is shown set forth in SEQ ID NO: 19. Preferred mutated antibodies comprise a heavy chain variable region comprising an amino acid sequence selected from the group consisting of SEQ ID NOs: 34, 35, 36 and 37. Preferably, the antibody VH chain is paired with the VK chain of 13H5, as set forth in SEQ ID NO: 22.

Methods of Engineering Antibodies

As discussed above, the anti-IFN alpha antibodies having VH and VL sequences disclosed herein can be used to create new anti-IFN alpha antibodies by modifying the VH and/or VL sequences, or the constant region(s) attached thereto. Thus, in another aspect of the invention, the structural features of an anti-IFN alpha antibody of the invention, e.g. 13H5, 13H7 or 7H9, are used to create structurally related anti-IFN alpha antibodies that retain at least one functional property of the antibodies of the invention, such as binding to IFN alpha. For example, one or more CDR regions of 13H5, 13H7 or 7H9, or mutations thereof, can be combined recombinantly with known framework regions and/or other CDRs to create additional, recombinantly-engineered, anti-IFN alpha antibodies of the invention, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-IFN alpha antibody comprising:

(a) providing: (i) a heavy chain variable region antibody sequence comprising a CDR1 amino acid sequence selected from the group consisting of SEQ ID NOs: 1, 2 and 3; and/or a CDR2 amino acid sequence selected from the group consisting of SEQ ID NOs: 4, 5, and 6; and/or a CDR3 amino acid sequence selected from the group consisting of SEQ ID NOs: 7, 8, and 9; and/or (ii) a light chain variable region antibody sequence comprising a CDR1 amino acid sequence selected from the group consisting of SEQ ID NOs: 10, 11, and 12; and/or a CDR2 amino acid sequence selected from the group consisting of SEQ ID NOs: 13, 14, and 15; and/or a CDR3 amino acid sequence selected from the group consisting of SEQ ID NOs: 13, 14, and 15;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-IFN alpha antibodies described herein, which functional properties include, but are not limited to:

(i) inhibiting the biological activity of interferon alpha;
(ii) inhibiting the biological activity of multiple IFN alpha subtypes but not substantially inhibiting the biological activity of IFN alpha 21;
(iii) not substantially inhibiting the biological activity of IFN beta or IFN omega;

(iv) inhibiting IFN-induced surface expression of CD38 or MHC Class on peripheral blood mononuclear cells;

(v) inhibiting IFN-induced expression of IP-10 by peripheral blood mononuclear cells;

(vi) inhibiting dendritic cell development mediated by systemic lupus erythematosus (SLE) plasma;

(vii) binding to human interferon alpha 2a with high affinity;

(viii) binding to human interferon alpha 2b with high affinity.

The functional properties of the altered antibodies can be assessed using standard assays available in the art and/or described herein. For example, the ability of the antibody to bind IFN alpha can be determined using standard binding assays, such as those set forth in the Examples (e.g., ELISAs and/or Biacores). The ability of the antibody to inhibit various functional activities of interferon alpha can be determined using assays such as those described in the Examples (e.g., Daudi cell proliferation, IFN-induced cell marker expression, IFN-induced IP-10 expression etc.)

In certain embodiments of the methods of engineering antibodies of the invention, mutations can be introduced randomly or selectively along all or part of an anti-IFN alpha antibody coding sequence (e.g., 13H5 coding sequence) and the resulting modified anti-IFN alpha antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the invention are those encoding the $V_H$ and $V_L$ sequences of the 13H5, 13H7, or 7H9 monoclonal antibodies. DNA sequences encoding the $V_H$ sequences of 13H5, 13H7, and 7H9 are shown in SEQ ID NOs: 25, 26, and 27, respectively. DNA sequences encoding the $V_L$ sequences of 13H5, 13H7, and 7H9 are shown in SEQ ID NOs: 28, 29, and 30, respectively.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CK. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the $V_H$- and $V_L$-encoding DNA fragments are operatively linked to another fragment encoding a flexible linker, e.g., encoding the amino acid sequence $(Gly_4\text{-}Ser)_3$, such that the $V_H$ and $V_L$ sequences can be expressed as a contiguous single-chain protein, with the $V_L$ and $V_H$ regions joined by the flexible linker (see e.g., Bird et al, (1988) *Science* 242:423-426; Huston et al. (1988) *Proc. Natl. Acad. Sci. USA* 85:5879-5883; McCafferty et al., (1990) *Nature* 348:552-554).

Production of Monoclonal Antibodies of the Invention

Monoclonal antibodies (mAbs) of the present invention can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against IFN alpha can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et at (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchromosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-IFN alpha antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-IFN alpha antibodies of the invention. For example, mice carrying both a human heavy chain transchromosome and a human light chain transchromosome, referred to as "TC mice" can be used; such mice are described in Tomizuka et al. (2000) *Proc. Natl. Acad. Set. USA* 97:722-727. Furthermore, cows carrying human heavy and light chain transchromosomes have been described in the art (Kuroiwa et al. (2002) *Nature Biotechnology* 20:889-894) and can be used to raise anti-IFN alpha antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the invention, such mice can be immunized with a purified or recombinant preparation of IFN alpha antigen, as described by Lonberg, N. et al. (1994) *Nature* 368(6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a purified preparation of lymphoblastoid IFN (25-100 µg), prepared by treating a lymphoblastoid cell line with virus such that the cell line produces an IFN alpha preparation containing multiple IFN alpha subtypes (but not IFN omega) can be used to immunize the human Ig mice intraperitoneally. Alternatively, mixtures of recombinant forms of IFN alpha subtypes can be used as the immunogen.

Detailed procedures to generate fully human monoclonal antibodies to IFN alpha are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-IFN alpha human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. For HuMab mice, usually both HCo7 and HCo12 strains are used. In addition, both HCo7 and HCo12 transgene can be bred together into a single mouse having two different human heavy chain transgenes (HCo7/HCo12). Alternatively or additionally, the KM mouse strain can be used, as described in Example 2.

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.), Eluted IgG can be checked by gel electrophoresis and high performance liquid chromatography to ensure purity. The buffer solution can be exchanged into PBS, and the concentration can be determined by OD280 using 1.43 extinction coefficient, The monoclonal antibodies can be aliquoted and stored at −80° C.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) *Science* 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector, Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques, The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the invention can be tested for binding to IFN alpha by, for example, standard ELISA or by Biacore analysis. Briefly, for ELISAs, microliter plates are coated with IFN alpha (e.g., the recombinant form of different IFN alpha subtypes, or leukocyte or lymphoblastoid IFN) at 0.25 μg/ml in PBS, and then blocked with 5% bovine serum albumin in PBS. Dilutions of antibody (e.g., dilutions of plasma from IFN alpha-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with IFN alpha immunogen. Hybridomas that bind with high avidity to IFN alpha are subcloned and further characterized. One clone from each hybridoma, which retains the reactivity of the parent cells (by ELISA), can be chosen for making a 5-10 vial cell bank stored at −140° C., and for antibody purification.

To purify anti-IFN alpha antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-IFN alpha monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using WN alpha coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 μg/ml of anti-human immunoglobulin overnight at 4° C., After blocking with 1% BSA, the plates are reacted with 1 μg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-IFN alpha human IgGs can be further tested for reactivity with IFN alpha antigen by Western blotting. Briefly, cell extracts from cells expressing IFN alpha can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Immunoconjugates

In another aspect, the present invention features an anti-IFN alpha antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins," A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites methotrexate, 6-mercaptopurine, 6-thioguanine, cytarabine, 5-fluorouracil decarbazine), alkylating agents mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R, J, (2002) *Curr. Opin. Investig. Drugs* 3:1089-1091; Senter, P. D. and Springer, C. J. (2001) *Adv. Drug Deity. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Method for preparing radioimmunoconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et at, "Monoclonal Antibodies For Immunotargeting Of Drugs In Cancer Therapy", in Monoclonal Antibodies And Cancer Therapy, Reisfeld er al. (eds.), pp. 243-56 (Alan R. Liss, Inc, 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et at (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific molecules comprising an anti-IFN alpha antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for IFN alpha and a second binding specificity for a second target epitope. In a particular embodiment of the invention, the second target epitope is an Fc receptor, e.g., human FcγRI (CD64) or a human Fcα receptor (CD89). Therefore, the invention includes bispecific molecules capable of binding both to FcγR, FcαR or FcεR expressing effector cells (e.g., monocytes, macrophages or polymorphonuclear cells (PMNs)), and to target cells expressing IFN alpha. These bispecific molecules target IFN alpha expressing cells to effector cell and trigger Fc receptor-mediated effector cell activities, such as phagocytosis of an IFN alpha expressing cells, antibody dependent cell-mediated cytotoxicity (ADCC), cytokine release, or generation of superoxide anion.

In an embodiment of the invention in which the bispecific molecule is multispecific, the molecule can further include a third binding specificity, in addition to an anti-Fc binding specificity and an anti-IFN alpha binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the $F_c$ receptor or target cell antigen, The "anti-enhancement factor portion" can bind an $F_c$ receptor or a target cell antigen. Alternatively, the anti-enhancement factor portion can bind to an entity that is different from the entity to which the first and second binding specificities bind, For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII (CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ M$^{-1}$).

The production and characterization of certain preferred anti-Fcγ monoclonal antibodies are described by Fanger et al, in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. H139469. In other embodiments, the anti-Fcγ receptor antibody is a humanized form of monoclonal antibody 22 (H22). The production and characterization of the H22 antibody is described in Graziano, R. F. et al. (3995) *J. Immunol* 155 (10): 4996-5002 and PCT Publication WO 94/10332. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5\times10^7$ M$^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148: 1764).

FcαRI and FcγRI are preferred trigger receptors for use in the bispecific molecules of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self antigens, targeted to them.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-IFN alpha binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160: 1686; Liu, M A et al, (1985) *Proc. Natl. Acad. Sci. USA*

82:8648). Other methods include those described in Paulus (1985) Behring Ins. Mitt. No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co, (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-IFN alpha antibody of the present invention combined with at least one other anti-IFN alpha agent (e.g., an immunosuppressing agent).

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-IFN alpha antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 3-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-IFN alpha antibody of the invention preferably results in a decrease in severity of disease symptoms, an increase in frequency and duration of disease symptom-free periods, or a prevention of impairment or disability due to the disease affliction. For example, in the case of systemic lupus erythematosus (SLE), a therapeutically effective dose preferably prevents further deterioration of physical symptoms associated with SLE, such as, for example, pain or fatigue. A therapeutically effective dose preferably also prevents or delays onset of SLE, such as may be desired when early or preliminary signs of the disease are present. Likewise it includes delaying chronic progression associated with SLE. Laboratory tests utilized in the diagnosis of SLE include chemistries (including the measurement of IFN alpha levels), hematology, serology and radiology. Accordingly, any clinical or biochemical assay that monitors any of the foregoing may be used to determine whether a particular treatment is a therapeutically effective dose for treating SLE. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods of the Invention

Monoclonal anti-IFN alpha antibodies and related derivatives/conjugates and compositions of the present invention have a variety of in vitro and in vivo diagnostic and therapeutic utilities. For example, the antibodies can be used to detect IFN alpha protein, either in vitro or in vitro, using standard antibody/antigen binding assays (e.g., ELISA, RIA). Furthermore, these molecules can be administered to a subject, e.g., in vivo, to treat, prevent or diagnose a variety of disorders in which IFN alpha plays a role. As used herein, the term "subject" is intended to include both human and nonhuman animals. Preferred subjects include human patients exhibiting autoimmune disorders. The term "nonhuman animals" of the invention includes all vertebrates, e.g., mammals and non-mammals, such as nonhuman primates, sheep, dog, cat, cow, horse, chickens, amphibians, reptiles, etc.

The antibody compositions of the invention can be used in the treatment of autoimmune diseases, such as systemic lupus erythematosus (SLE), multiple sclerosis (MS), inflammatory bowel disease (IBD; including Crohn's Disease, Ulcerative Colitis and Celiac's Disease), insulin dependent diabetes mellitus (IDDM), psoriasis, autoimmune thyroiditis, rheumatoid arthritis (RA) and glomerulonephritis. Furthermore, the antibody compositions of the invention can be used for inhibiting or preventing transplant rejection or in the treatment of graft versus host disease (GVHD).

Antibodies of the invention can be initially tested for binding activity associated with therapeutic use in vitro. For example, compositions of the invention can be tested using Biacore, ELISA and flow cytometric assays described in the Examples below. Moreover, the activity of these molecules can be assayed, for example, by a cell proliferation assay following exposure to IFN alpha, as described in the Examples below. Suitable methods for administering antibodies and compositions of the present invention are well known in the art, and are described further above. Suitable dosages also can be determined within the skill in the art and will depend on the age and weight of the subject and the particular drug used. Exemplary dosages are described further above.

Anti-IFN alpha antibodies of the invention also can be co-administered with other therapeutic agents as described above.

As noted above, for purposes of therapy, a human antibody composition and a pharmaceutically acceptable carrier are administered to a patient in a therapeutically effective amount. A combination of an antibody composition and a pharmaceutically acceptable carrier is said to be administered in a "therapeutically effective amount" if the amount administered is physiologically significant. An agent is "physiologically significant" if its presence results in a detectable change in the physiology of a recipient patient. A targeted therapeutic agent is "therapeutically effective" if it delivers a higher proportion of the administered dose to the intended target than accrues at the target upon systemic administration of the equivalent untargeted agent.

Also within the scope of the invention are kits comprising the compositions (e.g., human antibodies, immunoconjugates and bispecific molecules) of the invention and instructions for use. The kit can further contain a least one additional reagent, such as one or more additional human antibodies of the invention (e.g., a human antibody having a complementary activity which inhibits IFN alpha activity but that is distinct from the first human antibody).

The present invention is further illustrated by the following examples which should not be construed as further limiting. The contents of all figures and all references, patents and published patent applications cited throughout this application are expressly incorporated herein by reference.

EXAMPLES

Example 1

Generation of Human Monoclonal Antibodies Against IFN Alpha

Antigen:

Natural human IFNα containing multiple sub-types purified from a virally-stimulated human lymphoblastoid cell line, resulting in production of multiple IFN alpha subtypes but not IFN omega, was used as the antigen.

Transgenic Transchromosomic KM Mice™:

Fully human monoclonal antibodies to IFN alpha were prepared using the KM strain of transgenic transchromosomic mice, which expresses human antibody genes. In this mouse strain, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187 for HuMab mice. The mouse carries a human kappa light chain transgene, KCo5, as described in Fishwild et al. (1996) *Nature Biotechnology* 14:845-851. The mouse also carries a human heavy chain transchromosome, SC20, as described in PCT Publication WO 02/43478.

KM Mouse™ Immunizations:

To generate fully human monoclonal antibodies to IFN alpha, KM Mice™ were immunized with natural human IFNα containing multiple sub-types purified from a virally-stimulated human lymphoblastoid cell line. General immunization schemes are described in Lonberg, N. et al. (1994) *Nature* 368: 856-859; Fishwild, D. et al. (1996) *Nature Biotechnology* 14: 845-851 and PCT Publication WO 98/24884. The mice were 6-16 weeks of age upon the first infusion of antigen. A purified natural preparation (25-100 μg) of IFN alpha antigen (i.e., purified from virally stimulated lymphoblastoid cells) was used to immunize the KM Mice™ intraperitonealy (IP) or subcutaneously (Sc).

Transgenic transchromosomic mice were immunized intraperitonealy (IP) or subcutaneously (Sc) with antigen in complete Freund's adjuvant twice, followed by 2-4 weeks IP immunization (up to a total of 8 immunizations) with the antigen in incomplete Freund's adjuvant. The immune response was monitored by retroorbital bleeds. The plasma was screened by ELISA (as described below), and mice with sufficient titers of anti-IFNα human immunoglobulin were used for fusions. Mice were boosted intravenously with antigen 3 and 2 days before sacrifice and removal of the spleen.

Selection of KM Mice™ Producing Anti-IFNα Antibodies:

To select KM mice producing antibodies that bound IFNα, sera from immunized mice were tested by ELISA as described by Fishwild, D. et al. (1996). Briefly, microliter plates were coated with purified natural IFNα from lymphoblastoid cells at 1-2 μg/ml in PBS, 50 μl/well, incubated 4° C. overnight then blocked with 200 μl/well of 5% chicken serum in PBS/Tween (0.05%). Dilutions of plasma from IFNα immunized mice were added to each well and incubated for 1-2 hours at ambient temperature. The plates were washed with PBS/Tween and then incubated with a goat-anti-human IgG Fc polyclonal antibody conjugated with horseradish peroxidase (HRP) for 1 hour at room temperature. After washing, the plates were developed with ABTS substrate (Sigma, A-1888, 0.22 mg/ml) and optical density for each well was determined using a spectrophotometer set to wavelength 415 nm with a background correction at 495 nm. Mice that developed the highest titers of anti-IFNα antibodies were used for fusions. Fusions were performed as described below and hybridoma supernatants were tested for anti-IFNα activity by ELISA.

Generation of Hybridomas Producing Human Monoclonal Antibodies to IFNα:

Splenocytes were isolated from KM Mice™ and fused to a mouse myeloma cell line based upon standard protocols using PEG. The resulting hybridomas were then screened for the production of antigen-specific antibodies.

Single cell suspensions of splenic lymphocytes from immunized mice were fused to one-fourth the number of P3X63-Ag8.653 nonsecreting mouse myeloma cells (ATCC, CRL 1580) or SP2/0 nonsecreting mouse myeloma cells (ATCC, CRL 1581) using 50% PEG (Sigma). Cells were plated at a density of about $1 \times 10^5$/well in flat bottom microtiter plates and incubated approximately 2 weeks in selective medium containing 10% fetal bovine serum, 10% P388D1 (ATCC, CRL T1B-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamicin and 1×HAT (Sigma, CRL P-7185). After 1-2 weeks, cells were cultured in medium in which the HAT was replaced with HT. Individual wells were then screened by ELISA (described above) for human anti-IFNα IgG antibodies.

Conditioned medium from the antibody secreting hybridomas identified by ELISA was tested in a Daudi proliferation assay (described below) for the capacity to block the antiproliferative effects of IFNα. The hybridomas with highest neutralizing activity in the Daudi assay screen were subcloned at least twice by limiting dilution. The resulting stable subclones were then cultured in vitro to generate small amounts of monoclonal antibody in tissue culture medium. The Daudi proliferation assay screen was repeated to confirm the activity of the sub-clones. The sub-clones with highest activity in the Daudi assay were scaled up to produce sufficient conditioned medium (typically 1 L) for purification of monoclonal anti-IFNα for further characterization.

Screen of Hybridomas for Neutralizing Anti-IFNα Antibody: Daudi Proliferation Assay:

Interferon alpha inhibits the proliferation of Daudi (Burkitts lymphoma, ATCC #CCL-213) cells in a dose dependant manner. A neutralizing antibody, which blocks interferon binding to its receptor, will restore proliferation. Dose response curves for the anti-proliferative effects of natural lymphoblastoid IFNα on Daudi were determined and a concentration sufficient to inhibit Daudi growth by 50% (EC50) was calculated.

Hybridoma conditioned medium was mixed with Daudi cells in culture medium (RPMI 1640 supplemented with 10% FCS, 1×2-ME, L-glutamine and penicillin streptomycin) with and without the addition of IFNα in a 96 well, flat-bottomed cell culture plate. The final mixture of reagents was as follows: $1 \times 10^4$ Daudi cells+10% hybridoma supernate+/−IFNα at EC50 per 100 ul/well. The cells were incubated at 37° C., 5% $CO_2$, 72 hrs. Proliferation was assayed with the addition of MTS (Promega), 20 ul/well and O.D. at 490 nm was read following a further 3 hrs incubation. The viable cell number was proportional to the O.D. reading. Percentage Daudi inhibition was calculated for hybridoma supernate+IFNα relative to hybridoma supernate alone and compared to a media control with and without IFNα. Hybridomas were rank ordered according to the potency of IFNα blockade and the most active neutralizing hybridomas were selected for sub-cloning.

Hybridoma clones 13H5, 13H7 and 7H9 were selected for further analysis.

Example 2

Structural Characterization of Human Monoclonal Antibodies 13H5, 13H7 and 7H9

The cDNA sequences encoding the heavy and light chain variable regions of the 13H5, 13H7, and 7H9 monoclonal antibodies were obtained from the 13H5, 13H7, and 7H9 hybridomas, respectively, using standard PCR techniques and were sequenced using standard DNA sequencing techniques.

The nucleotide and amino acid sequences of the heavy chain variable region of 13H5 are shown in FIG. 1A and in SEQ ID NO: 25 and 19, respectively.

The nucleotide and amino acid sequences of the light chain variable region of 13H5 are shown in FIG. 1B and in SEQ ID NO: 28 and 22, respectively.

Comparison of the 13H5 heavy chain immunoglobulin sequence to the known human germline immunoglobulin heavy chain sequences demonstrated that the 13H5 heavy chain utilizes a $V_H$ segment from human germline VH 1-18, an undetermined D segment, and a $J_H$ segment from human germline $J_H$ 4b. The alignment of the 13H5 $V_H$ sequence to the germline VH 1-18 sequence is shown in FIG. 4. Further analysis of the 13H5 $V_H$ sequence using the Kabat system of CDR region determination led to the delineation of the heavy chain CDR1, CDR2 and CD3 regions as shown in FIGS. 1A and 4, and in SEQ ID NOs: 1, 4 and 7, respectively.

Comparison of the 13H5 light chain immunoglobulin sequence to the known human germline immunoglobulin light chain sequences demonstrated that the 131-15 light chain utilizes a $V_L$ segment from human germline VK A27 and a JK segment from human germline JK 1. The alignment of the 13H5 $V_L$ sequence to the germline VK A27 sequence is shown in FIG. 6. Further analysis of the 13H5 $V_L$ sequence using the Kabat system of CDR region determination led to the delineation of the light chain CDR1, CDR2 and CD3 regions as shown in FIGS. 1B and 6, and in SEQ ID NOs: 10, 13 and 16, respectively.

The nucleotide and amino acid sequences of the heavy chain variable region of 13H7 are shown in FIG. 2A and in SEQ ID NO: 26 and 20, respectively.

The nucleotide and amino acid sequences of the light chain variable region of 13H7 are shown in FIG. 2B and in SEQ ID NO: 29 and 23, respectively.

Comparison of the 13H7 heavy chain immunoglobulin sequence to the known human germline immunoglobulin heavy chain sequences demonstrated that the 13H7 heavy chain utilizes a $V_H$ segment from human germline VH 4-61, a D segment from human germline 3-10, and a $J_H$ segment from human germline $J_H$ 4b. The alignment of the 13H7 $V_H$ sequence to the germline VH 4-61 sequence is shown in FIG. 5. Further analysis of the 13H7 $V_H$ sequence using the Kabat system of CDR region determination led to the delineation of the heavy chain CDR1, CDR2 and CD3 regions as shown in FIGS. 2A and 5, and in SEQ ID NOs: 2, 5 and 8, respectively.

Comparison of the 13H7 light chain immunoglobulin sequence to the known human germline immunoglobulin light chain sequences demonstrated that the 13H7 light chain utilizes a $V_L$ segment from human germline VK A27 and a JK (segment from human germline JK 2. The alignment of the 13H7 $V_L$ sequence to the germline VK A27 sequence is shown in FIG. 6. Further analysis of the 13H7 $V_L$ sequence using the Kabat system of CDR region determination led to the delineation of the light chain CDR1, CDR2 and CD3 regions as shown in FIGS. 2B and 6, and in SEQ ID NOs: 11, 14 and 17, respectively.

The nucleotide and amino acid sequences of the heavy chain variable region of 7H9 are shown in FIG. 3A and in SEQ ID NO: 27 and 21, respectively.

The nucleotide and amino acid sequences of the light chain variable region of 7H9 are shown in FIG. 3B and in SEQ ID NO: 30 and 24, respectively.

Comparison of the 7H9 heavy chain immunoglobulin sequence to the known human germline immunoglobulin heavy chain sequences demonstrated that the 7H9 heavy chain utilizes a $V_H$ segment from human germline VH 1-18, a D segment from human germline 6-6, and a $J_H$ segment from human germline $J_H$ 4b. The alignment of the 7H9 $V_H$ sequence to the germline VH 1-18 sequence is shown in FIG. 4. Further analysis of the 7H9 $V_H$ sequence using the Kabat system of CDR region determination led to the delineation of the heavy chain CDR1, CDR2 and CD3 regions as shown in FIGS. 3A and 4, and in SEQ ID NOs: 3, 6 and 9, respectively.

Comparison of the 7H9 light chain immunoglobulin sequence to the known human germline immunoglobulin light chain sequences demonstrated that the 7H9 light chain utilizes a $V_L$ segment from human germline VK A27 and a JK segment from human germline JK 1. The alignment of the 7H9 $V_L$ sequence to the germline VK A27 sequence is shown in FIG. 6. Further analysis of the 7H9 $V_1$ sequence using the Kabat system of CDR region determination led to the delineation of the light chain CDR1, CDR2 and CD3 regions as shown in FIGS. 3B and 6, and in SEQ ID NOs:12, 15 and 18, respectively.

Example 3

Anti-IFN Alpha Human Monoclonal Antibodies Inhibit the Biological Activity of Multiple Interferon Alpha Subtypes As described in Example 1, interferon alpha inhibits the proliferation of Daudi (Burkitts lymphoma, ATCC #CCL- 213) cells in a dose dependant manner. A neutralizing antibody, which blocks interferon binding to its receptor, will restore proliferation. Using this cell proliferation assay, the specificity of the purified human anti-IFN alpha antibodies was examined by testing for blockade of natural lymphoblastoid IFNα, natural leukocyte interferon, 13 recombinant IFN alpha subtypes, IFN beta and IFN omega.

Daudi cells were grown in culture medium (RPM 1640 supplemented with 10% FCS, 1×2-ME, L-glutamine and penicillin streptomycin) with and without the addition of IFNα in a 96 well, flat-bottomed cell culture plate. Each type 1 interferon tested was assayed at $EC_{50}$ and mixed with a 2-fold serial titration of each antibody, typically from 50 ug/ml (312 nM) through 381 pg/ml (2.4 pM). The antibody/IFN mixture was added to Daudi cells in a 96-well bottomed plate to a final density of $1 \times 10^4$ Daudi cells/100 ul/well and incubated at 37° C., 5% $CO_2$, 72 hrs. Proliferation was assayed with the addition of MTS (Promega), 20 µl/well, and O.D. at 490 nm was measured following a further 3 hour incubation. The viable cell number was proportional to the O.D. reading. Percentage blockade of interferon was calculated relative to Daudi proliferation in the absence of IFN (=100% blockade) and in the presence of IFN alone (=0% blockade). Antibodies were scored according to the degree of blockade, resulting in a profile of IFNα subtype specificity for each antibody tested. An $EC_{50}$ was derived with PRISM™ software using non-linear regression; sigmoidal dose response; variable slope curve fit. The results demonstrated that the human anti-IFN alpha antibody 13H5 inhibits the action of multiple interferon alpha subtypes, particularly, IFNα 6, 2b, 2a, 1, 16, 10, 8, 5 and 14, but not IFNα 21, IFNβ or IFNω. 13H5 is a low level inhibitor of TEN alpha subtypes 17, 7 and 4. The $EC_{50}$ values and % blockade of interferon are shown in table 1, below.

TABLE 1

Antibody Inhibition of Multiple IFN Alpha Subtypes 13H5 IFN Blockade

| IFN | EC50 | 1000x |
|---|---|---|
| Lymphoblastoid IFN | 127 pM | 82% |
| IFNα 6 | 208 pM | 95% |
| IFNα 2b | 432 pM | 80% |
| IFNα 2a | 448 pM | 95% |
| IFNα 1 | 4.6 nM | 68% |
| Leukocyte IFN | 5.5 nM | 70% |
| IFNα 16 | 6.8 nM | 80% |
| IFNα 10 | 19.6 nM | 40% |
| IFNα 8 | 26 nM | 37% |
| IFNα 5 | 56 nM | 47% |
| IFNα 14 | 70 nM | 34% |
| IFNα 17 | 110 nM | 13% |
| IFNα 7 | >300 nM | 15% |
| IFNα 4 | >300 nM | 7% |
| IFNα 21 | >300 nM | NS |
| IFN-beta | >300 nM | NS |
| IFN-omega | >300 nM | NS |

NS = not significant

Example 4

Inhibition of IFN Alpha Induction of Cell Surface Markers by Anti-IFN Alpha Antibodies The addition of IFN alpha 2b to cell culture media is known to induce the expression of the cell surface markers CD38 and MHC Class I on normal peripheral blood mononuclear cells (PBMNC). The activity of human anti-IFN alpha antibody 13H5 was tested for inhibition of interferon induced cell surface marker expression on cultures of primary human cells and assayed by FACS analysis.

The anti-IFNα monoclonal antibody 13H5 and isotype controls were diluted to 20 ug/ml each in PBMNC culture medium (RPMI 1640+10% FBS+1% human serum). Antibody was dispensed 1.5 ml/well into T25 vented cap culture flasks and mixed with an equal volume of either 400 iu/ml leukocyte IFN, IFN alpha 2b or IFN ω, diluted in culture medium or with medium alone. PBMNC were isolated from normal human blood using heparin coated Vacutainer® CPT™ tubes according to manufacturer recommendations (Becton Dickinson & Co). Cells were resuspended in culture medium (RPMI 1640+10% FBS+1% human serum) to $2 \times 10^6$ cells/ail and were added in equal volume to the Ab/IFN mixtures such that the final assay contains; $6 \times 10^6$ PBMNC+5 ug/ml Ab+/−100 iu/ml IFN per 6 ml medium. Flasks were incubated at 37° C., 5% $CO_2$ for 24 or 48 hrs.

Conditioned medium was harvested from each flask and suspension cells were recovered by centrifugation at 1000 rpm on a Sorvall RTH-750 rotor. The pelleted cells were retained on ice and supernate was frozen at −80° C. for ELISA. Adherent cells were recovered from the flask with a PBS wash (2 ml), followed by 15 minute incubation in versene (3 ml). The flask was scraped at the end of the versene incubation and the flask was finally rinsed with PBS wash (2 ml). Each of the PBS washes and the versene was combined with the cells recovered from conditioned medium harvest. The pooled cell suspension was centrifuged at 1000 rpm on a Sorvall RTH-750 rotor, the resulting pellet was resuspended to 300 ul in staining buffer (PBS+0.1M EDTA+2% FBS+1% HS) and dispensed 100 ul/well into a V-bottom 96-well plate.

The plate was pulse-centrifuged at 2800 rpm on a Sorvall RTH-750 rotor and pelleted cells were resuspended 250 well in fluorochrome labeled antibodies as follows: (1) mouse anti-MHC I-FITC+mouse anti-CD38-PE, and (2) isotype controls, mouse IgG-FITC+mouse IgG-PE. The plate was incubated on ice for 45 minutes, protected from light. The cells were washed three times with the addition of 200 µl staining buffer followed by pulse-celtrifugation and finally resuspended in 200 µl of 2% paraformaldehyde in PBS. Staining of monocyte cells was analyzed by flow cytometry with the Becton Dickinson FACScalibur™, gates were drawn on the Forward Scatter vs. Side Scatter graph to remove contaminating cells from the analysis. The results demonstrated that the human monoclonal antibody 13H5 inhibits leukocyte IFN and recombinant IFNα 2b induced changes in expression of CD38 and MHC Class I on normal PBMNC. The human monoclonal antibody 13H5 does not block IFNω mediated changes in the cell surface marker expression of CD38 and MHC Class I. These results are shown in Tables 2 and 3 below.

TABLE 2

| | Percent Change in IFN-Induced MHC Class I Expression on Normal PBMNC | | |
|---|---|---|---|
| Ab Treatment | Leukocyte IFN (100 u/ml) | IFN alpha 2b (100 u/ml) | IFN omega (100 u/ml) |
| No antibody | 31 | 21 | 28 |
| 13H5 (5 µg/ml) | −1 | −1 | 29 |
| Control Ig (5 µg/ml) | 16 | 25 | 26 |

TABLE 3

Percent Change in IFN-Induced
CD38 Expression on Normal PBMNC

| Ab Treatment | Leukocyte IFN (100 u/ml) | IFN alpha 2b (100 u/ml) | IFN omega (100 u/ml) |
|---|---|---|---|
| No antibody | 774 | 426 | 782 |
| 13H5 (5 µg/ml) | 195 | 16 | 760 |
| Control Ig (5 µg/ml) | 614 | 392 | 829 |

Example 5

Inhibition of IFN-Induction Expression of IP-10 by Anti-IFN Alpha Antibodies

The addition of IFN alpha 2b to cell culture media is known to induce IP-10 expression in normal peripheral blood mononuclear cells (PBMNC). The activity of human anti-IFN alpha antibody 13H5 was tested for inhibition of interferon induced expression of IP-10 in normal PBMNC cultures by an ELISA binding assay.

A PBMNC culture was prepared as described in Example 4, conditioned with leukocyte IFN, IFN alpha 2b, or IFN ω. Conditioned medium was analyzed for IP-10/CXCL10 expression using a quantitative sandwich ELISA kit (Quantikine®, R&D Systems) at a 1:30 dilution according to manufacturer recommendations. The results demonstrated that the human monoclonal antibody 13H5 inhibits leukocyte IFN and recombinant IFNα 2b induced expression of IP-10 in normal PBMNC culture but does not block IFNω induced IP-10 expression. These results are shown in Table 4.

TABLE 4

Antibody Inhibition of in IFN-Induced
IP-10 Expression on Normal PBMNC

| Ab Treatment | No IFN | Leukocyte IFN (100 u/ml) | IFN alpha 2b (100 u/ml) | IFN omega (100 u/ml) |
|---|---|---|---|---|
| No antibody | 907 | 2665 | 2739 | 2904 |
| 13H5 (5 µg/ml) | 946 | 1765 | 1262 | 3862 |
| Control Ig (5 µg/ml) | 838 | 3512 | 3117 | 3960 |

Example 6

Affinity Characterization of Anti-IFN Alpha Human Monoclonal Antibody

In this example, the monoclonal antibody 13E5 was examined for binding affinity of recombinant IFN alpha 2a and IFN alpha 2b using Biacore analysis, Purified antibodies at 10 ug/ml, were captured on a CM5 chip coated with Prot-G. Concentrations of antigen from 80 µM to 10 nM in HBS-EP running buffer was passed aver the chip at a rate of 25 ul/min. The association time allowed was 5 minutes, followed by a 10 minute dissociation period. Background and non-specific binding of antigen to both the chip and antibodies was eliminated by detecting the binding to surface with captured isotype control human-IgG (Sigma) and buffer. Regeneration of the chip was achieved with a flow rate of 100 ul/min for 0.4 minutes using 20 mM NaOH 400 mM NaCl. The association and dissociation curves were fit to a Langmuir binding model using BIAevaluation software (Biacore AB). The results are shown below in Table 5.

TABLE 5

Binding Characteristics of Monoclonal Antibody 13H5

| IFN Alpha Subtype | $K_D$ | $K_{on}$ | $K_{off}$ |
|---|---|---|---|
| IFN Alpha 2a | $1.0 \times 10^{-10}$ M | $3.3 \times 10^{-5}$ 1/Ms | $3.5 \times 10^{-5}$ 1/Ms |
| IFN Alpha 2b | $1.0 \times 10^{-10}$ M | $5.1 \times 10^{-5}$ 1/Ms | $5.3 \times 10^{-5}$ 1/Ms |

Example 7

Antibody Inhibition of SLE Plasma Mediated Dendritic Cell Development

SLE plasma induces dendritic cell development from normal human monocytes. In this example, purified monoclonal human anti-IFN alpha antibodies were tested for inhibition of dendritic cell development, as assessed by the ability of the antibodies to inhibit the induction of the cell surface markers CD38, MHC Class I and CD123 by SLE plasma.

A 25 ml buffy coat was diluted four fold with PBS. The sample was separated into 4×50 ml conical tubes, and 15 ml of lymphocyte separation medium (ICN Biomedicals) was layered underneath. Following a 30-minute spin at 500×g, the buffy layer containing the PBMCs was removed and washed with PBS. Cells were resuspended in culture media at $4 \times 10^6$ cells/ml. Monocytes were isolated by incubating PBMC ($2.0 \times 10^7$ cells/5 ml/25 cm$^2$ flask) for 1.5 hrs at 37° C. in culture medium and then washing away non-adherent cells twice. Following the second wash the cells were cultured in media containing 1% heat inactivated human serum. Twenty five percent SLE patient plasma plus/minus neutralizing antibodies and isotype controls (30 ug/ml) were added to the culture flasks; IFN alpha 2b (100 & 10 iu/ml) plus 25% normal human plasma was used as a positive control for marker induction. Flasks were incubated at 37° C., 5% $CO_2$ for three to seven days. Dendritic cells were then recovered from conditioned medium, with PBS and versene treatment if necessary, before being stained as described for blockade of marker induction in PBMNC culture (as described in Example 4 above). Staining of dendritic cells was analyzed by flow cytometry with the Becton Dickinson FACScalibur™. Gates were drawn on the Forward Scatter vs. Side Scatter graph to remove contaminating cells from the analysis. The anti-IFN alpha human monoclonal antibody 13H5 inhibits the IFN alpha dependent process of dendritic cell development, as demonstrated by normalized expression of cell surface markers MHC Class I, CD38, and CD123 in the presence of 13H5. The results are shown below in Table 6, wherein (A), (B), (C) & (D) summarize results for four representative SLE donor samples.

TABLE 6

Inhibition of Dendritic Cell Maturation (A)

| | Donor Plasma 40 (13 iu/ml IFN) | | |
|---|---|---|---|
| Culture Cond | MHC I | CD123 | CD38 |
| 0 IFN | 148.34 | 14.22 | 39.78 |
| 10 iu/ml IFNa 2b | 199.84 | 18.92 | 44.18 |
| 100 iu/ml IFNa 2b | 229.05 | 26.27 | 63.36 |
| 0 Ab | 206.02 | 22 | 46.78 |
| 13H5 | 144.92 | 13.67 | 35.11 |
| Control IgG | 193.52 | 21.5 | 62.04 |

TABLE 6-continued

Inhibition of Dendritic Cell Maturation (B)

| | Donor Plasma 39 (19 iu/ml IFN) | | |
|---|---|---|---|
| Culture Cond | MHC I | CD123 | CD38 |
| 0 IFN | 248.83 | 18.63 | 32.69 |
| 10 iu/ml IFNa 2b | 331.82 | 21.42 | 63.23 |
| 100 iu/ml IFNa2b | 430.87 | 30.56 | 60.61 |
| 0 Ab | 443.21 | 17.53 | 44.87 |
| 13H5 | 330.59 | 14.18 | 20.56 |
| Control IgG | 432.43 | 17.88 | 39.33 |

('C)

| | Donor Plasma 36 | | |
|---|---|---|---|
| Culture Cond | MHC I | CD123 | CD38 |
| 0 IFN | 358.88 | 15.25 | 45.75 |
| 10 iu/ml IFNa 2b | 457.133 | 17.41 | 58.48 |
| 100 iu/ml IFNa 2b | 496.32 | 20.63 | 64.55 |
| 0 Ab | 488.58 | 28.92 | 88.31 |
| 13H5 | 429.31 | 15.44 | 73.88 |
| Control IgG | 485.7 | 19.75 | 115.18 |

(D)

| | Donor Plasma 59 (75 iu/ml IFN) | | |
|---|---|---|---|
| Culture Cond | MHC I | CD123 | CD38 |
| 0 IFN | 228.96 | 10.5 | 58 |
| 10 iu/ml IFNa 2b | 271.19 | 11.95 | 86.49 |
| 100 iu/ml IFNa 2b | 293.99 | 12.73 | 112.49 |
| 0 Ab | 202.04 | 14.74 | 61.61 |
| 13H5 | 127.22 | 9.17 | 30.79 |
| Control IgG | 266 | 14.4 | 55.46 |

Example 8

Mechanism of Action of Monoclonal Antibody 13H5

In this example, several binding experiments using radiolabeled cytokine and antibody with IFNAR expressing cells were conducted in order to determine the mechanism of action for 13H5.

In the first set of experiments, recombinant IFNα, 2a was radio-iodinated with a specific activity of 29.3 Ci/mmole (Pierce IODO-GEN® tubes) and was determined to specifically bind Daudi cells with a $K_D$ of approximately 1 nM. To examine competition binding of this ligand to cells, glass fiber plates were blocked with 200 μl/well milk buffer overnight at 4° C. Daudi cells were dispensed at 2×10⁶ cells/well in RPM 1640 medium and were mixed with $^{125}$I-IFNα (2 nM), plus a 3-fold dilution series of competitor, either 13H5, an isotype control antibody or unlabelled IFNα (30 nM to 14 pM). The plate was incubated 2 hours at 4° C. on a shaker before being washed with RPMI and air-dried. The filters were transferred to glass tubes and analyzed for radioactivity.

Representative results from several experiments are shown in FIG. 7. Unlabeled ligand was used as a positive control and was observed to specifically block $^{125}$I-IFNα binding with an $IC_{50}$ of approximately 0.5 nM. The 13H5 antibody, however, did not block binding of iodinated ligand but was instead observed to enhance the radioactive signal associated with treated cells, contrasting with the behavior of the isotype control antibody, which had no effect on $^{125}$I-IFNα binding to cells. This result indicates that 13H5 has a non-competitive mechanism of action and neutralizes biological activity by blockade of signaling but not by blockade of ligand binding.

The above result also suggested that 13H5 may become associated with the cell surface in the presence of IFNα. Since each 13H5 molecule has the capacity to bind two IFNα molecules, it is possible that these events would also result in a second ligand being linked to the cell membrane. This hypothesis is supported by the observation that cell-associated radioactivity was enhanced approximately 2-fold at concentrations of antibody and ligand consistent with a 1:1 ratio of IFNα to 13E5 binding sites.

Figure 8:
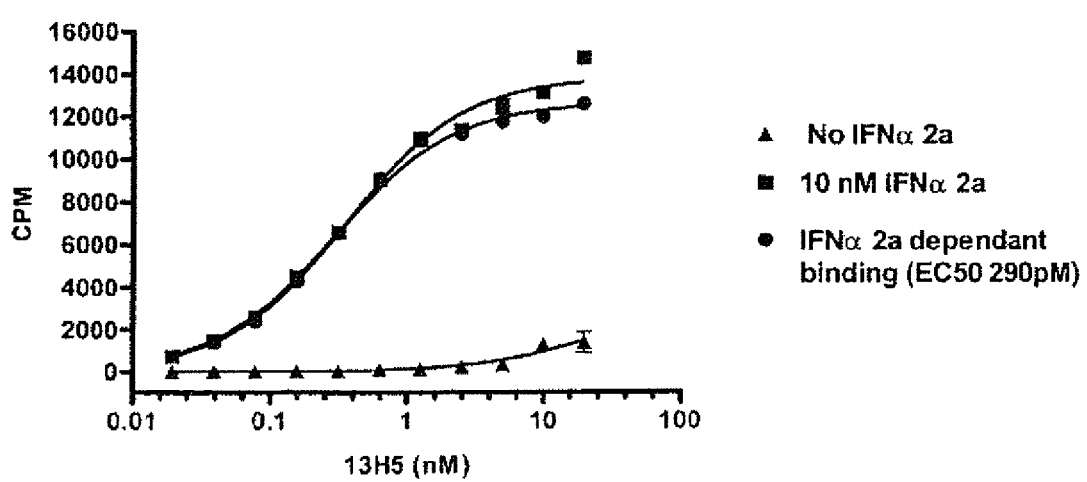
FIG. 8 is a graph showing binding of $^{125}$I-13H5 to Daudi cells in the presence of IFNα 2a (■) but not in the absence of IFNα 2a (▲). Specific IFNα-dependent binding of 13H5 is represented by circles (•).

To further examine the mechanism of action of 13H5, the binding of the antibody to Daudi cells was assayed using radiolabeled antibody in the presence or absence of IFNα 2a. The cytokine was used at a concentration (10 nM) calculated to saturate IFNAR binding based upon earlier binding studies. The 13H5 antibody was radio-iodinated with a specific activity of 414 Ci/mmole (Pierce IODO-GEN® tubes). To examine antibody binding to cells, glass fiber plates were blocked with 200 μl/well milk buffer overnight at 4° C. Daudi cells were dispensed at 2×10⁶ cells/well in RPMI 1640 medium and were mixed with a 2-fold dilution series of $^{125}$-13H5 (20 nM to 20 pM), plus/minus IFNα 2a (10 nM). The plate was incubated 2 hours at 4° C. on a shaker before being washed with RPMI and air-dried. The filters were transferred to glass tubes and analyzed for radioactivity. CPM values measured for $^{125}$-13H5 binding alone were subtracted from those measured in the presence of IFNα 2a in order to determine IFNα 2a dependent binding. Representative results from several experiments are shown in FIG. 8. The results showed dose dependant saturable binding of $^{125}$-13H5 to Daudi cells in the presence of IFNα 2a but negligible binding with $^{125}$-13H5 alone. The specific IFNα-dependent binding of 13H5 is represented in FIG. 8 by circles and was calculated by subtracting CPM for antibody alone (representing non-specific binding) from total CPM for 13H5 binding in the presence of IFNα.

Thus, in summary, the mechanism of action of 13H5 is a non-competitive one in which the complex of IFNα bound to 13H5 is capable of binding to IFNAR on the cell surface and the biological activity of IFNα is neutralized by blockade of signaling through IFNAR.

Example 9

Antibody Dependent Cell-Mediated Cytotoxicity Assays with 13H5

Since 13H5 can associate with the cell surface in the presence of IFNα, antibody dependent cell-mediated cytotoxicity (ADCC) was investigated using a $^{51}$Cr-release assay. Raji cells were used as targets for lysis by fresh human mononuclear cells. Mononuclear cells were purified from heparinized whole blood by Flea Hypaque density centrifugation. Target cells were labeled with 100 μCi of $^{51}$Cr per 10⁶ cells for 1 hour prior to dispensing into U-bottom microtiter plates, 10⁴ cells per well, and combining with effector cells (effector: target ratio=50:1) plus titrations of antibody. Following 4 hours incubation at 37° C., supernatant conditioned medium was collected and analyzed for radioactivity. Release of radioactivity in the absence of antibody was used as a control for background and detergent treatment of target cells was used to determine 100% lysis. Cytotoxicity was calculated by the formula: % lysis=(experimental cpm−target leak cpm)/(detergent lysis cpm−target leak cpm)×100%. Specific lysis=% lysis with 13H5−% lysis without 13H5. Assays were performed in triplicate.

Figure 9:
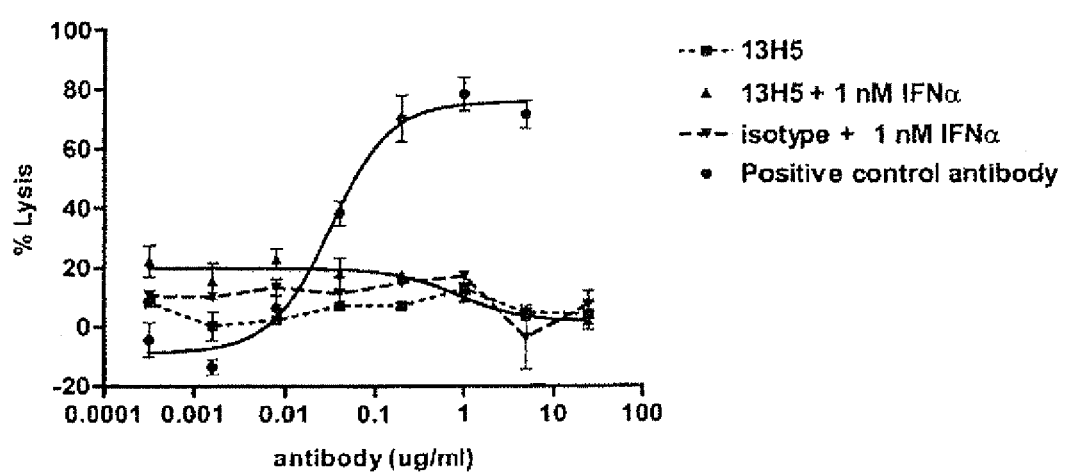
FIG. 9 is a graph showing the results of ADCC assays of Raji cell lysis by fresh human mononuclear cells in the presence of 13H5 (■), 13H5 IFNα (▲), an isotype control antibody+IFNα (▼), or a positive control antibody (•). Lysis was only seen with the positive control.

The results of the ADCC assay, summarized in FIG. 9, demonstrate that 13H5 had no significant ADCC activity on Raji cells, either alone or in the presence of IFNα 2b, Similarly, an isotype matched IgG displayed no activity, whereas the positive control (Rituximab) exhibited robust dose dependent cytotoxicity. These results indicate that IFNα mediated association of 13H5 with the cell surface of IFNAR expressing cells is not sufficient to mediate ADCC.

Example 10

Examination of Stability of 13H5

The 13H5 antibody contains a potential deamidation site at Asn-55 in the CDR2 region of the heavy chain. Deamidation of asparagines residues is a common modification of polypeptides and proteins obtained using recombinant DNA technology and may result in decreased biological activity and/or stability, though deamidation does not always correlate with loss of biological activity. Deamidation of asparagines to form aspartic acid (and iso-Asp) results in a change of net charge, which can be detected by charge-based analytical methods. To examine deamidation of 13H5 under accelerated conditions (basic pH), methods for detection of deamidated variants of Fab fragment by IEX-HPLC and capillary isoelectric focusing (cEIF) were used.

To accelerate deamidation of 13H5, the antibody was exposed to buffer at alkaline pH. For the starting material, a 102 µl aliquot of 13H5 (at 5.9. mg/ml for a total of 600 µg) was added to 498 µl of PBS and 6 µl of 100× sodium azide stock (2% solution). For the time zero PBS sample, 130 µl of starting material was combined with 30 µl of PBS and the sample was placed at −20° C. until further analysis. For the time zero sample in deamidation buffers, 130 µl of starting material was combined with 15 µl of 10× deamidation buffer (10% ammonium bicarbonate, pH 8.5) and 15 µl of pH adjustment buffer (1M MES, pH 6.0) and placed at −20° C. until further analysis. For the Day 2 sample in PBS, 130 µl of starting material was combined with 30 µl of PBS and incubated at 40° C. for 48 hours and then the sample was placed at −20° C. until further analysis. For the Day 2 sample under deamidation conditions, 130 µl of starting material was combined with 15 µl of 10× deamidation buffer and incubated at 40° C. for 48 hours. After 48 hours, 15 µl of pH adjustment buffer was added and the sample was placed at −20° C. until further analysis.

To prepare the above samples for analysis, papain digestion was performed. Reaction conditions used were: 160 µl of sample (130 µg 13H5), 3.2 µl of 50 mM cysteine and 6.5 µl of papain enzyme at 1.0 mg/ml in solution. The samples were placed at 40° C. for 4 hours and the reaction was stopped by addition of 4.8 µl of 1M iodoacetamide. After papain digestion, non-reducing SDS-PAGE was performed to confirm the presence of Fab and Fc fragments.

To perform IEX-HPLC on the samples, all samples were first dialyzed against water for 3 hours. Then, 50 µl of each sample was applied to HPLC with the following chromatography conditions:
  Column=Dionex WCX-10 weak cation exchange column
  "A" buffer=10 mM MES, pH 5.5
  "B" buffer=10 mM MES, pH 5.5; 1.0 M NaCl
  Elution=4-25% "B" over 30 minutes at 0.8 ml/min
  Detection=UV absorbance at 280 nM
The results of TEX-HPLC analysis are summarized in Table 7 below, which shows the peak areas for deamidated Fab for time zero and Day 2 samples under deamidation conditions:

TABLE 7

| Sample | Peak Area Deamidated Fab | (% peak area) Deamidated Fab | Peak Area Fab | (% peak area) Fab | Total Peak Area |
|---|---|---|---|---|---|
| Time 0 | 89,244 | 6.13 | 1,366,233 | 93.87 | 1,455,477 |
| Day 2 | 459,759 | 43.95 | 586,428 | 56.01 | 1,046,187 |

To perform cIEF analysis, samples were first dialyzed against water for 3 hours and then applied to cIEF using standard methods of analysis. The results of cIEF analysis are summarized in Table 8 below, which shows the peak areas for deamidated Fab for time zero and Day 2 samples under deamidation conditions:

TABLE 8

| Sample | Peak Area Deamidated Fab | (% peak area) Deamidated Fab | Peak Area Fab | (% peak area) Fab | Total Peak Area |
|---|---|---|---|---|---|
| Time 0 | 75,902 | 13.96 | 467,987 | 86.04 | 543,889 |
| Day 2 | 251,317 | 58.81 | 176,040 | 41.19 | 427,357 |

To examine the pH dependence of forced deamidation, the IEX-HPLC data for the Day 2 sample in PBS (pH 7.0) was compared to the Day 2 sample under deamidation conditions. The results are summarized in Table 9 below, which shows the peak areas for the deamidated Fab for Day 2 PBS and Day 2 under deamidation conditions:

TABLE 9

| Sample | Peak Area Deamidated Fab | (% peak area) Deamidated Fab | Peak Area Fab | (% peak area) Fab | Total Peak Area |
|---|---|---|---|---|---|
| PBS | 106,344 | 7.0 | 1,413,233 | 93.0 | 1,519,577 |
| deamidated | 459,759 | 43.95 | 586,428 | 56.01 | 1,046,187 |

This data supports the existing theory of protein degradation, which predicts that deamidation of polypeptides via beta-aspartyl shift mechanism occurs at an increased rate under basic pH as compared to neutral pH.

Example 11

Preparation and Characterization of 13115 Mutants with Enhanced Stability

In this example, 13H5 mutants were prepared having an amino acid substitution at Asn-55 and the stability of these mutants was examined, at Day 2 under forced deamidation conditions, by cIEF analysis as described in Example 10. The mutants were prepared by standard recombinant DNA mutagenesis techniques. The sequences of the mutants at amino acid positions 55-58 of $V_H$, as compared to wild type 13H5, were as follows:

```
13H5 wild-type:
                               (SEQ ID NO: 41)
N G N T

Mutant #1:
                               (SEQ ID NO: 38)
D G N T

Mutant #2:
                               (SEQ ID NO: 39)
Q G N T

Mutant #3:
                               (SEQ ID NO: 40)
Q G Q T
```

The full-length $V_H$ amino acid sequences of mutants #1, #2 and #3 are shown in SEQ ID NOs: 34, 35 and 36, respectively.

The results of the cIEF analysis are shown below in Table 10, which shows the peak areas for deamidated Fab for the wild type and mutants at Day 2 deamidation conditions:

TABLE 10

| Sample | Peak Area Deamidated Fab | (% peak area) Deamidated Fab | Peak Area Fab | (% peak area) Fab | Total Peak Area |
|---|---|---|---|---|---|
| 13H5 wild type | 24,065 | 54.2 | 20,304 | 45.8 | 44,369 |
| Mutant 1 | 10,382 | 9.7 | 96,584 | 90.3 | 106,966 |
| Mutant 2 | 4,592 | 8.0 | 52,460 | 92.0 | 57,052 |
| Mutant 3 | 7,733 | 8.9 | 79,077 | 91.1 | 86,810 |

The results demonstrate that each of the three Asn-55 mutants exhibits greater stability under forced deamidation conditions than the wild-type 13H5 antibody.

SUMMARY OF SEQUENCE LISTING

| SEQ ID NO: | SEQUENCE |
|---|---|
| 1 | VH CDR1 a.a. 13H5 |
| 2 | VH CDR1 a.a. 13H7 |
| 3 | VH CDR1 a.a. 7H9 |
| 4 | VH CDR2 a.a. 13H5 |
| 5 | VH CDR2 a.a. 13H7 |
| 6 | VH CDR2 a.a. 7H9 |
| 7 | VH CDR3 a.a. 13H5 |
| 8 | VH CDR3 a.a. 13H7 |
| 9 | VH CDR3 a.a. 7H9 |
| 10 | VK CDR1 a.a. 13H5 |
| 11 | VK CDR1 a.a. 13H7 |
| 12 | VK CDR1 a.a. 7H9 |
| 13 | VK CDR2 a.a. 13H5 |
| 14 | VK CDR2 a.a. 13H7 |
| 15 | VK CDR2 a.a. 7H9 |
| 16 | VK CDR3 a.a. 13H5 |
| 17 | VK CDR3 a.a. 13H7 |
| 18 | VK CDR3 a.a. 7H9 |
| 19 | VH a.a. 13H5 |
| 20 | VH a.a. 13H7 |
| 21 | VH a.a. 7H9 |
| 22 | VK a.a. 13H5 |
| 23 | VK a.a. 13H7 |
| 24 | VK a.a. 7H9 |
| 25 | VH n.t. 13H5 |
| 26 | VH n.t. 13H7 |
| 27 | VH n.t. 7H9 |
| 28 | VK n.t. 13H5 |
| 29 | VK n.t. 13H7 |
| 30 | VK n.t. 7H9 |
| 31 | VH 1-18 germline a.a. |
| 32 | VH 4-61 germline a.a. |
| 33 | VK A27 germline a.a. |
| 34 | VH a.a. 13H5 N55D mut. |
| 35 | VH a.a. 13H5 N55Q mut. |
| 36 | VH a.a. 13H5 N55Q mut. N57Q mut. |
| 37 | VH a.a. 13H5 G56A mut. |

What is claimed is:

1. An isolated nucleic acid encoding a heavy chain variable region and a light chain variable region of an anti-interferon alpha antibody, or antigen-binding portion thereof, said variable regions comprising:
    (a) a heavy chain variable region comprising amino acids having the sequence set forth in SEQ ID NO:19; and a light chain variable region comprising amino acids having the sequence set forth in SEQ ID NO:22;

(b) a heavy chain variable region comprising amino acids having the sequence set forth in SEQ ID NO:20; and a light chain variable region comprising amino acids having the sequence set forth in SEQ ID NO:23;

(c) a heavy chain variable region comprising amino acids having the sequence set forth in SEQ ID NO:21; and a light chain variable region comprising amino acids having the sequence set forth in SEQ ID NO:24; or (d) a heavy chain variable region comprising amino acids having the sequence set forth in SEQ ID NO: 34, 35, 36 or 37; and a light chain variable region comprising amino acids having the sequence set forth in SEQ ID NO:22.

2. An isolated nucleic acid encoding:

a) a heavy chain variable region of an anti-interferon alpha monoclonal antibody, or antigen-binding portion thereof, comprising amino acids having the sequence of: SEQ ID NO:19, SEQ ID NO:20, SEQ ID NO:21, SEQ ID NO:34, SEQ ID NO:35, SEQ ID NO:36 or SEQ ID NO:37; or b) a light chain variable region of an anti-interferon alpha monoclonal antibody, or antigen-binding portion thereof, comprising amino acids having the sequence of: SEQ ID NO:22, SEQ ID NO:23, or SEQ ID NO:24.

3. An isolated nucleic acid encoding:
   a) a heavy chain variable region of an anti-interferon alpha monoclonal antibody, or antigen-binding portion thereof, said nucleic acid comprising nucleotides having the sequence of: SEQ ID NO:25, SEQ ID NO:26, or SEQ ID NO:27; or
   b) a light chain variable region of an anti-interferon alpha monoclonal antibody, or antigen-binding portion thereof, said nucleic acid comprising nucleotides having the sequence of: SEQ ID NO:28, SEQ ID NO:29, or SEQ ID NO:30.

4. An expression vector comprising the nucleic acid of claim 2.

5. A host cell expressing a polypeptide encoded by the nucleic acid of claim 2.

6. The nucleic acid of claim 2, wherein the anti-interferon alpha antibody, or antigen-binding portion thereof comprises: (a) a heavy chain variable region comprising amino acids having the sequence set forth in SEQ ID NO:19; and (b) a light chain variable region comprising amino acids having the sequence set forth in SEQ ID NO:22.

7. The nucleic acid of claim 2, wherein the anti-interferon alpha antibody, or antigen-binding portion thereof comprises: (a) a heavy chain variable region comprising amino acids having the sequence set forth in SEQ ID NO:20; and (b) a light chain variable region comprising amino acids having the sequence set forth in SEQ ID NO:23.

8. The nucleic acid of claim 2, wherein the anti-interferon alpha antibody, or antigen-binding portion thereof comprises: (a) a heavy chain variable region comprising amino acids having the sequence set forth in SEQ ID NO:21; and (b) a light chain variable region comprising amino acids having the sequence set forth in SEQ ID NO:24.

9. The nucleic acid of claim 2, wherein the anti-interferon alpha antibody, or antigen-binding portion thereof comprises: (a) a heavy chain variable region comprising amino acids having the sequence set forth in SEQ ID NO: 34, 35, 36 or 37; and (b) a light chain variable region comprising amino acids having the sequence set forth in SEQ ID NO:22.

10. The nucleic acid of claim 3, which encodes a heavy chain variable region of an anti-interferon alpha monoclonal antibody, or antigen-binding portion thereof, comprising amino acids having the sequence of: SEQ ID NO:19, SEQ ID NO:20, SEQ ID NO:21, SEQ ID NO:34, SEQ ID NO:35, SEQ ID NO:36 or SEQ ID NO:37.

11. The nucleic acid of claim 3, which encodes a light chain variable region of an anti-interferon alpha monoclonal antibody, or antigen-binding portion thereof, comprising amino acids having the sequence of: SEQ ID NO:22, SEQ ID NO:23, or SEQ ID NO:24.

12. The nucleic acid of claim 3, which encodes (a) a heavy chain variable region of an anti-interferon alpha monoclonal antibody, or antigen-binding portion thereof comprising amino acids having the sequence set forth in SEQ ID NO:19; or (b) a light chain variable region of an anti-interferon alpha monoclonal antibody, or antigen-binding portion thereof comprising amino acids having the sequence set forth in SEQ ID NO:22.

13. The nucleic acid of claim 3, which encodes (a) a heavy chain variable region of an anti-interferon alpha monoclonal antibody, or antigen-binding portion thereof comprising amino acids having the sequence set forth in SEQ ID NO:20; or (b) a light chain variable region of an anti-interferon alpha monoclonal antibody, or antigen-binding portion thereof comprising amino acids having the sequence set forth in SEQ ID NO:23.

14. The nucleic acid of claim 3, which encodes (a) a heavy chain variable region of an anti-interferon alpha monoclonal antibody, or antigen-binding portion thereof comprising amino acids having the sequence set forth in SEQ ID NO:21; or (b) a light chain variable region of an anti-interferon alpha monoclonal antibody, or antigen-binding portion thereof comprising amino acids having the sequence set forth in SEQ ID NO:24.

15. The nucleic acid of claim 3, which encodes (a) a heavy chain variable region of an anti-interferon alpha monoclonal antibody, or antigen-binding portion thereof comprising amino acids having the sequence set forth in SEQ ID NO: 34, 35, 36 or 37; or (b) a light chain variable region of an anti-interferon alpha monoclonal antibody, or antigen-binding portion thereof comprising amino acids having the sequence set forth in SEQ ID NO:22.

16. The nucleic acid of claim 4, which encodes a heavy chain variable region of an anti-interferon alpha monoclonal antibody, or antigen-binding portion thereof, said nucleic acid comprising nucleotides having the sequence of: SEQ ID NO:25, SEQ ID NO:26, or SEQ ID NO:27.

17. The nucleic acid of claim 4, which encodes a light chain variable region of an anti-interferon alpha monoclonal antibody, or antigen-binding portion thereof, said nucleic acid comprising nucleotides having the sequence of: SEQ ID NO:28, SEQ ID NO:29, or SEQ ID NO:30.

18. The nucleic acid of claim 4, which encodes (a) a heavy chain variable region of an anti-interferon alpha monoclonal antibody, or antigen-binding portion thereof, said nucleic acid comprising nucleotides having the sequence set forth in SEQ ID NO:25, or (b) a light chain variable region of an anti-interferon alpha monoclonal antibody, or antigen-binding portion thereof, said nucleic acid comprising nucleotides having the sequence set forth in SEQ ID NO:28.

19. The nucleic acid of claim 4, which encodes (a) a heavy chain variable region of an anti-interferon alpha monoclonal antibody, or antigen-binding portion thereof, said nucleic acid comprising nucleotides having the sequence set forth in SEQ ID NO:26, or (b) a light chain variable region of an anti-interferon alpha monoclonal antibody, or antigen-binding portion thereof, said nucleic acid comprising nucleotides having the sequence set forth in SEQ ID NO:29.

20. The nucleic acid of claim 4, which encodes (a) a heavy chain variable region of an anti-interferon alpha monoclonal antibody, or antigen-binding portion thereof, said nucleic acid comprising nucleotides having the sequence set forth in SEQ ID NO:27, or (b) a light chain variable region of an anti-interferon alpha monoclonal antibody, or antigen-binding portion thereof, said nucleic acid comprising nucleotides having the sequence set forth in SEQ ID NO:30.

* * * * *

UNITED STATES PATENT AND TRADEMARK OFFICE
CERTIFICATE OF CORRECTION

| | |
|---|---|
| PATENT NO. | : 8,722,870 B2 |
| APPLICATION NO. | : 13/909608 |
| DATED | : May 13, 2014 |
| INVENTOR(S) | : Alison Witte et al. |

Page 1 of 2

It is certified that error appears in the above-identified patent and that said Letters Patent is hereby corrected as shown below:

IN THE CLAIMS:
At column 77, line 13:
"claim 2." should read
-- claim 1. --

At column 77, line 15:
"nucleic acid of claim 2." should read
-- nucleic acid of claim 1. --

At column 77, line 16:
"The nucleic acid of claim 2" should read
-- The nucleic acid of claim 1 --

At column 77, line 22:
"The nucleic acid of claim 2" should read
-- The nucleic acid of claim 1 --

At column 77, line 28:
"The nucleic acid of claim 2" should read
-- The nucleic acid of claim 1 --

At column 77, line 34:
"The nucleic acid of claim 2" should read
-- The nucleic acid of claim 1 --

At column 77, line 40:
"The nucleic acid of claim 3" should read
-- The nucleic acid of claim 2 --

Signed and Sealed this
Twenty-fourth Day of November, 2015

Michelle K. Lee
*Director of the United States Patent and Trademark Office*

IN THE CLAIMS:

At column 77, line 46:
"The nucleic acid of claim 3" should read
-- The nucleic acid of claim 2 --

At column 77, line 51:
"The nucleic acid of claim 3" should read
-- The nucleic acid of claim 2 --

At column 78, line 1:
"The nucleic acid of claim 3" should read
-- The nucleic acid of claim 2 --

At column 78, line 9:
"The nucleic acid of claim 3" should read
-- The nucleic acid of claim 2 --

At column 78, line 17:
"The nucleic acid of claim 3" should read
-- The nucleic acid of claim 2 --

At column 78, line 25:
"The nucleic acid of claim 4" should read
-- The nucleic acid of claim 3 --

At column 78, line 30:
"The nucleic acid of claim 4" should read
-- The nucleic acid of claim 3 --

At column 78, line 35:
"The nucleic acid of claim 4" should read
-- The nucleic acid of claim 3 --

At column 78, line 43:
"The nucleic acid of claim 4" should read
-- The nucleic acid of claim 3 --

At column 78, line 51:
"The nucleic acid of claim 4" should read
-- The nucleic acid of claim 3 --